United States Patent
Sasaki

(10) Patent No.: US 9,335,269 B2
(45) Date of Patent: May 10, 2016

(54) OPTICAL CONTROL DEVICE, CONTROL DEVICE, OPTICAL SCOPE, AND SCANNING OPTICAL DEVICE

(75) Inventor: Hiroshi Sasaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 929 days.

(21) Appl. No.: 13/488,633

(22) Filed: Jun. 5, 2012

(65) Prior Publication Data

US 2012/0242859 A1  Sep. 27, 2012

Related U.S. Application Data

(63) Continuation of application No. PCT/JP2010/071962, filed on Dec. 8, 2010.

(30) Foreign Application Priority Data

Dec. 15, 2009 (JP) .................... 2009-284472

(51) Int. Cl.
*G01N 21/64* (2006.01)
*A61B 1/06* (2006.01)
(Continued)

(52) U.S. Cl.
CPC ........ *G01N 21/6456* (2013.01); *A61B 1/00126* (2013.01); *A61B 1/00165* (2013.01);
(Continued)

(58) Field of Classification Search
CPC .. A61B 1/0638; A61B 1/0646; A61B 1/0005; G06T 2207/10068; G06T 2207/30101; H04N 5/2256; H04N 2005/2255
See application file for complete search history.

(56) References Cited

U.S. PATENT DOCUMENTS

2002/0138008 A1* 9/2002 Tsujita ............... A61B 1/00009
600/473
2006/0089554 A1 4/2006 Ishihara et al.
(Continued)

FOREIGN PATENT DOCUMENTS

JP 08-224209 9/1996
JP 09-308697 12/1997
(Continued)

OTHER PUBLICATIONS

Japanese Office Action dated Nov. 12, 2013 from related Japanese Patent Application No. 2009-284472, together with an English language translation.
(Continued)

*Primary Examiner* — Andy Rao
*Assistant Examiner* — Obafemi Sosanya
(74) *Attorney, Agent, or Firm* — Scully, Scott, Murphy & Presser, PC

(57) ABSTRACT

An optical control device is provided in a scanning optical device that applies light emitted from a light source to an observation target as spot light that is applied in a spot-like shape, and detects reflected light from the observation target while scanning with the spot light, the optical control device including an intensity enhancement section that enhances intensity of light within a specific wavelength band included in a wavelength band of white light emitted from a white light source, an irradiation section that applies specific wavelength band-enhanced white light to the observation target, the specific wavelength band-enhanced white light being white light for which intensity of light within the specific wavelength band is enhanced, and a light detection section that detects reflected light from the observation target when the irradiation section applies the specific wavelength band-enhanced white light to the observation target.

23 Claims, 19 Drawing Sheets

(51) Int. Cl.
- *A61B 1/07* (2006.01)
- *A61B 5/00* (2006.01)
- *A61B 1/04* (2006.01)
- *A61B 1/045* (2006.01)
- *A61B 1/00* (2006.01)

(52) U.S. Cl.
CPC .............. *A61B1/00172* (2013.01); *A61B 1/043* (2013.01); *A61B 1/0638* (2013.01); *A61B 1/0646* (2013.01); *A61B 1/0669* (2013.01); *A61B 1/07* (2013.01); *A61B 5/0071* (2013.01); *A61B 5/0084* (2013.01); *A61B 1/00009* (2013.01)

(56) References Cited

U.S. PATENT DOCUMENTS

| | | | |
|---|---|---|---|
| 2007/0153542 A1* | 7/2007 | Gono | A61B 1/0638 362/574 |
| 2007/0213593 A1 | 9/2007 | Nakaoka | |
| 2007/0276259 A1 | 11/2007 | Okawa et al. | |
| 2008/0058629 A1* | 3/2008 | Seibel | A61B 1/0008 600/368 |
| 2009/0244924 A1 | 10/2009 | Enomoto | |
| 2009/0306478 A1* | 12/2009 | Mizuyoshi | A61B 1/0638 600/178 |

FOREIGN PATENT DOCUMENTS

| | | |
|---|---|---|
| JP | 2003-14545 A | 1/2003 |
| JP | 2003-535659 | 12/2003 |
| JP | 2006-068113 | 3/2006 |
| JP | 2006-122234 | 5/2006 |
| JP | 2007-229053 | 9/2007 |
| JP | 2007-313169 | 12/2007 |
| JP | 2009-240635 | 10/2009 |
| WO | WO 01/97902 A2 | 12/2001 |

OTHER PUBLICATIONS

International Search Report dated Feb. 1, 2011 issued in PCT/JP2010/071962.

* cited by examiner

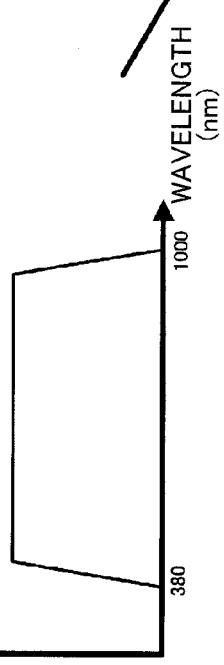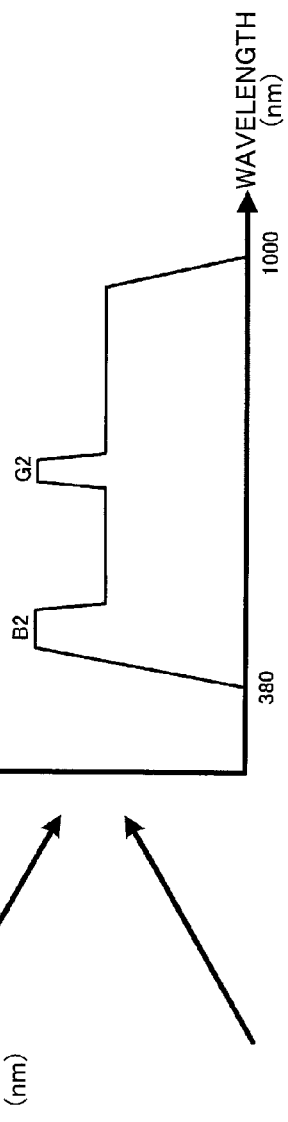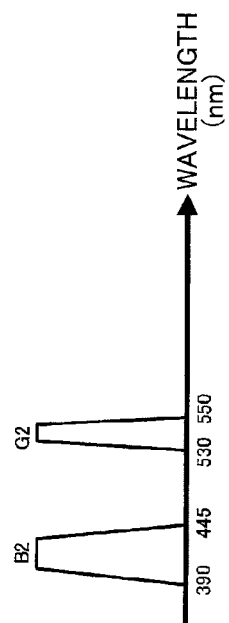

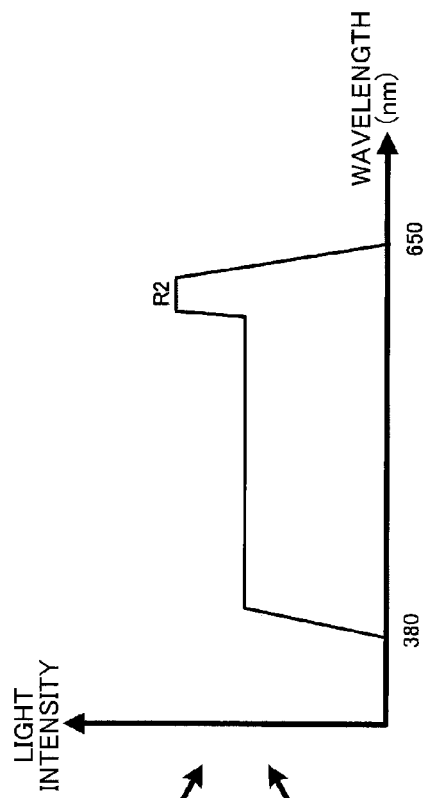
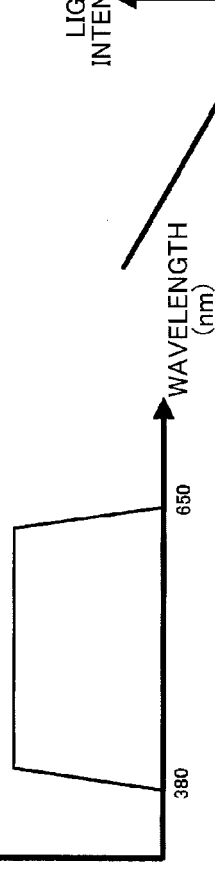
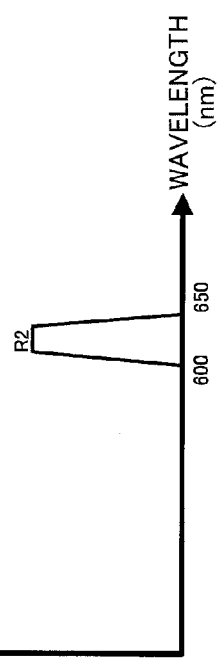

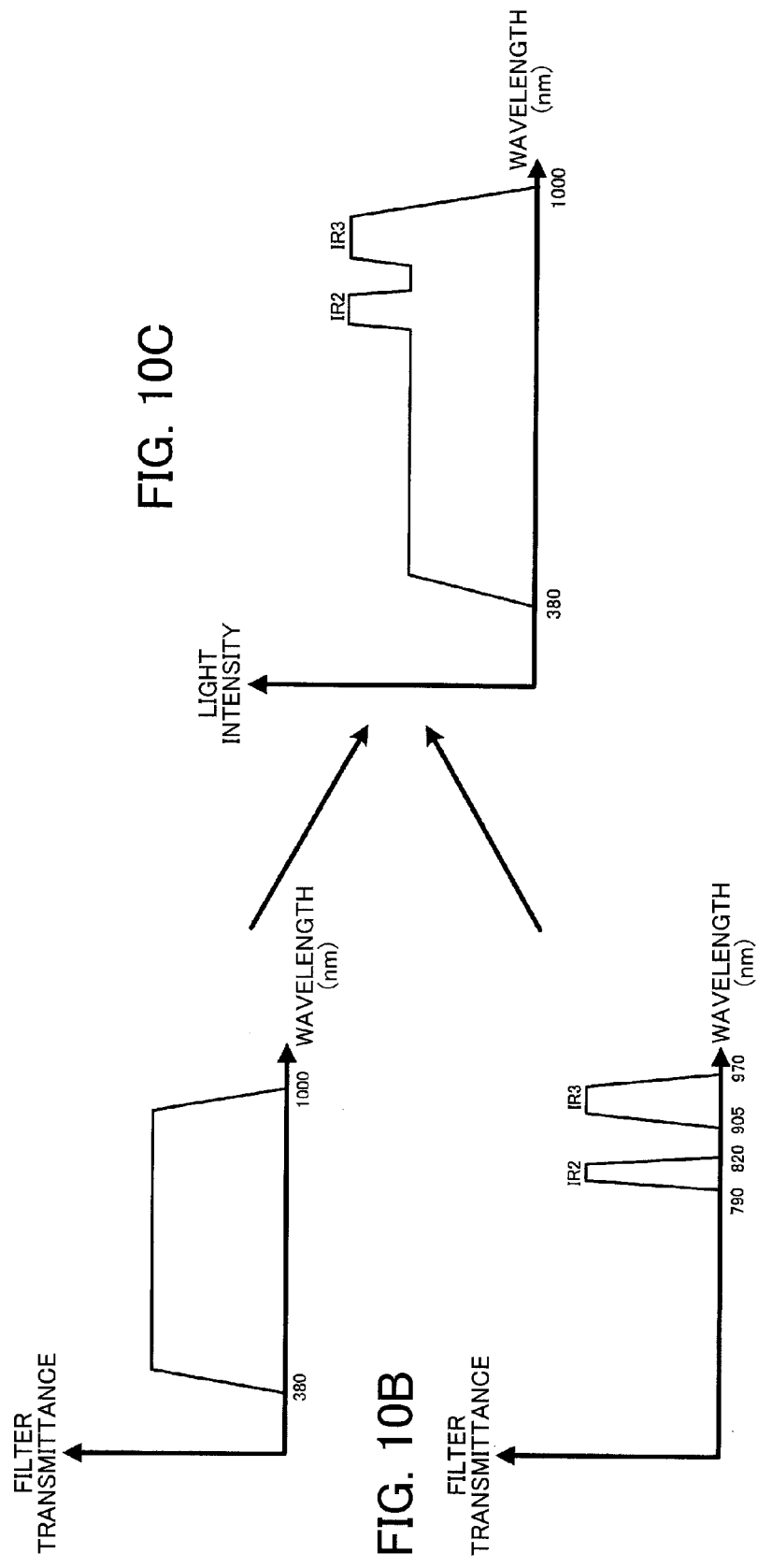

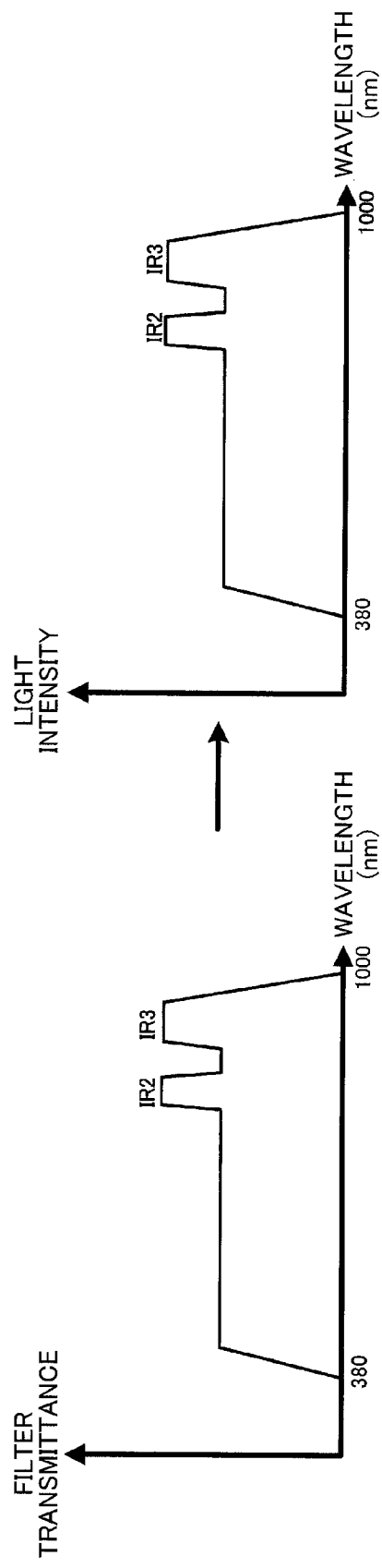

OPTICAL CONTROL DEVICE, CONTROL DEVICE, OPTICAL SCOPE, AND SCANNING OPTICAL DEVICE

CROSS REFERENCE TO RELATED APPLICATION

This application is a continuation of International Patent Application No. PCT/JP2010/071962, having an international filing date of Dec. 8, 2010, which designated the United States, the entirety of which is incorporated herein by reference. Japanese Patent Application No. 2009-284472 filed on Dec. 15, 2009 is also incorporated herein by reference in its entirety.

BACKGROUND

The present invention relates to an optical control device, a control device, an optical scope, a scanning optical device, and the like.

A frame-sequential endoscope system has been widely used. The frame-sequential endoscope system sequentially applies three colors of light (RGB) to tissue in a body cavity using a rotary filter, and allows the user to perform diagnosis using an image (normal light image) generated from reflected light images. An endoscope system has been proposed that sequentially applies two types of narrow-band light (G2 and B2) that differs in characteristics from the three colors of light to tissue in a body cavity, and allows the user to perform diagnosis using a narrow-band image generated from reflected light images (see JP-A-2006-68113, for example). An endoscope system has also been proposed that applies narrow-band excitation light to tissue in a body cavity, and allows the user to perform diagnosis using a fluorescent image generated by acquiring intrinsic fluorescence produced by the tissue or fluorescence produced by a fluorescent agent due to the excitation light (see JP-A-2007-229053, for example).

A dot-sequential scanning endoscope system that differs from the frame-sequential endoscope system has also been proposed. The dot-sequential scanning endoscope system applies spot light (including light having a UV wavelength, light having a visible wavelength, and light having an IR wavelength) to tissue in a body cavity from an optical fiber that is scanned at high speed, and receives reflected light to form an image. Since the scanning endoscope system is configured so that a light-receiving element can be provided outside a body, the size, number, and the like of the light-receiving elements are not basically limited. The spectral characteristics of the spot light can also be acquired by providing a spectroscope between the return light and the light-receiving elements. Moreover, a normal image, a fluorescent image, and the like can be generated based on the acquired spectral characteristics (see JP-A-2003-535659, for example).

SUMMARY

According to one aspect of the invention, there is provided an optical control device that is provided in a scanning optical device that applies light emitted from a light source to an observation target as spot light that is applied in a spot-like shape, and detects reflected light from the observation target while scanning with the spot light, the optical control device comprising:

an intensity enhancement section that enhances intensity of light within a specific wavelength band included in a wavelength band of white light emitted from a white light source;

an irradiation section that applies specific wavelength band-enhanced white light to the observation target, the specific wavelength band-enhanced white light being white light for which intensity of light within the specific wavelength band is enhanced by the intensity enhancement section; and a light detection section that detects reflected light from the observation target when the irradiation section applies the specific wavelength band-enhanced white light to the observation target.

According to another aspect of the invention, there is provided a scanning optical device that applies light emitted from a light source to an observation target as spot light that is applied in a spot-like shape, and detects reflected light from the observation target while scanning with the spot light, the scanning optical device comprising:

an intensity enhancement section that enhances intensity of light within a specific wavelength band included in a wavelength band of white light emitted from a white light source;

an irradiation section that applies specific wavelength band-enhanced white light to the observation target, the specific wavelength band-enhanced white light being white light for which intensity of light within the specific wavelength band is enhanced by the intensity enhancement section; and a light detection section that detects reflected light from the observation target when the irradiation section applies the specific wavelength band-enhanced white light to the observation target.

BRIEF DESCRIPTION OF THE DRAWINGS

FIGS. 8A, 8B, and 8C are views illustrating a specific wavelength band-enhanced white light acquisition method in an NBI mode.

FIGS. 9A, 9B, and 9C are views illustrating a specific wavelength band-enhanced white light acquisition method in a fluorescence imaging mode.

FIGS. 10A, 10B, and 10C are views illustrating a specific wavelength band-enhanced white light acquisition method in an IRI mode.

FIGS. 29A and 29B are views illustrating a specific wavelength band-enhanced white light acquisition method in an IRI mode.

DESCRIPTION OF EXEMPLARY EMBODIMENTS

Figure 1:
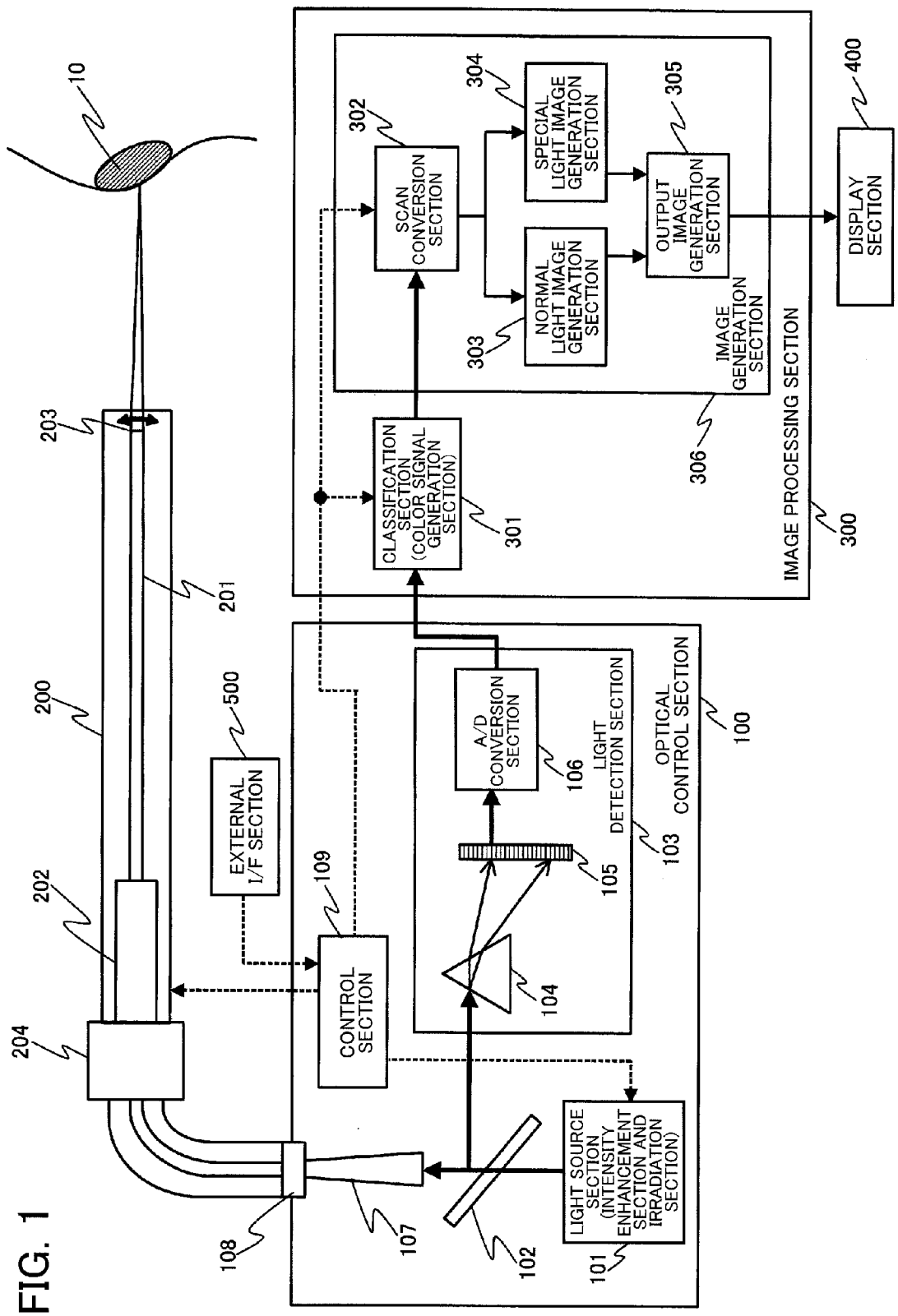
FIG. 1 illustrates a configuration example of a scanning optical device.

According to one embodiment of the invention, there is provided an optical control device that is provided in a scanning optical device that applies light emitted from a light source to an observation target as spot light that is applied in a spot-like shape, and detects reflected light from the observation target while scanning with the spot light, the optical control device comprising:

an intensity enhancement section that enhances intensity of light within a specific wavelength band included in a wavelength band of white light emitted from a white light source;

an irradiation section that applies specific wavelength band-enhanced white light to the observation target, the specific wavelength band-enhanced white light being white light for which intensity of light within the specific wavelength band is enhanced by the intensity enhancement section; and a light detection section that detects reflected light from the observation target when the irradiation section applies the specific wavelength band-enhanced white light to the observation target.

According to one embodiment of the invention, the specific wavelength band-enhanced white light for which the intensity of light within the specific wavelength band is enhanced, is acquired and applied, and the reflected light is detected. This makes it possible to improve the brightness of an image corresponding to the specific wavelength band, and generate a clear image.

According to another embodiment of the invention, there is provided a scanning optical device that applies light emitted from a light source to an observation target as spot light that is applied in a spot-like shape, and detects reflected light from the observation target while scanning with the spot light, the scanning optical device comprising:

an intensity enhancement section that enhances intensity of light within a specific wavelength band included in a wavelength band of white light emitted from a white light source;

an irradiation section that applies specific wavelength band-enhanced white light to the observation target, the specific wavelength band-enhanced white light being white light for which intensity of light within the specific wavelength band is enhanced by the intensity enhancement section; and a light detection section that detects reflected light from the observation target when the irradiation section applies the specific wavelength band-enhanced white light to the observation target.

According to this embodiment of the invention, the specific wavelength band-enhanced white light for which the intensity of light within the specific wavelength band is enhanced, is acquired and applied, and the reflected light is detected. This makes it possible to implement a scanning optical device that can improve the brightness of an image corresponding to the specific wavelength band, and generate a clear image.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

First Embodiment

An outline of a method according to a first embodiment of the invention is described below. When using a method that simultaneously acquires a normal light image and a special light image to observe a lesion area, since a lesion area is displayed in the special light image in a color differing from that of the peripheral area (e.g., a lesion such as epidermoid cancer is displayed in brown when using narrow band imaging), the visibility of the lesion area is improved as compared with observation using normal light. However, since the wavelength band of the special light is narrow, and the intensity of the special light is low as compared with observation using normal light, a dark image that is difficult to observe is obtained using the special light.

Several aspects of the invention propose a method that acquires a special light image that is bright and contains only a small amount of noise by increasing the intensity of light within a wavelength band corresponding to the special light. More specifically, light within a specific wavelength band (i.e., light that has been emitted from a white light source 501 and has passed through a filter 508 (see FIG. 2)) and white light (i.e., light that has been emitted from a white light source 503 (see FIG. 2)) are synthesized (combined), for example.

FIGS. 10A to 10C schematically illustrate the synthesis process. FIG. 10A illustrates the characteristics of a cut filter (barrier filter) 504. The intensity of light that has been emitted from the white light source 503 and has passed through the filter 504 has characteristics similar to the characteristics illustrated in FIG. 10A. FIG. 10B illustrates the characteristics of the filter 508. The intensity of light that has been emitted from the white light source 501 and has passed through the filter 508 has characteristics similar to the characteristics illustrated in FIG. 10B.

The above conditions are satisfied on the assumption that the intensity of light emitted from the white light source 501 is constant independently of the wavelength (i.e., the light source is an ideal light source). The following description is given on the assumption that the light source is an ideal light source so that the invention can be clearly understood. Note that the spectral radiant characteristics of an actual light source are not uniform, and the intensity of light that has passed the filter 508 is obtained by multiplying the characteristics of the filter 504 by the spectral radiant characteristics of the light source (i.e., precisely similar characteristics are not obtained).

The white light (see FIG. 10A) and the light within the specific wavelength band (see FIG. 10B) are synthesized at the position of a half mirror 510 (see FIG. 2) to acquire white light for which the specific wavelength band is enhanced (see FIG. 10C). A special light image that is bright and contains only a small amount of noise can be acquired while reducing the total irradiation energy by applying the white light for which the specific wavelength band is enhanced. The details of the above method are described in connection with the first embodiment.

Note that the white light for which the specific wavelength band is enhanced may be acquired by another method. The light source section and the like may be configured in a different way. Modifications will be described in detail in connection with a second embodiment and a third embodiment.

FIG. 1 illustrates a configuration example of a scanning optical device that implements the above method. The scanning optical device illustrated in FIG. 1 includes an optical control section 100, an insertion section 200, an image processing section 300, a display section 400, and an external I/F section 500. The optical control section 100 corresponds to an optical control device according to the first embodiment. A control device according to the first embodiment includes the optical control section 100 and the image processing section 300.

The optical control section 100 includes a light source section 101, a half mirror 102, a light detection section 103, a tapered rod 107, an optical connector 108, and a control section 109. Note that the configuration of the optical control section 100 is not limited thereto. Various modifications may be made, such as omitting some of these elements.

The insertion section 200 is formed to be elongated and flexible (i.e., can be curved) so that the insertion section 200 can be inserted into a body cavity, for example. The insertion section 200 includes an optical fiber 201, an actuator 202 that causes an emitting end 203 of the optical fiber 201 to vibrate, and an operation section 204 that allows the user to operate and control the flexible end of the insertion section 200. A piezoelectric element, a magnetostriction element, electromagnetic induction, or the like may be used as the actuator 202.

The image processing section 300 includes a classification section 301, a scan conversion section 302, a normal light image generation section 303, a special light image generation section 304, and an output image generation section 305. Note that the configuration of the image processing section 300 is not limited thereto. Various modifications may be made, such as omitting some of these elements.

The display section 400 is a display (e.g., CRT or liquid crystal monitor) that can display a moving picture (moving image).

The external I/F section 500 is an interface that allows the user to perform an input operation or the like on the scanning optical device. The external I/F section 500 includes a power switch (power ON/OFF switch), a mode (e.g., imaging (capturing) mode) switch button, and the like. The external I/F section 500 outputs input information to the control section 109.

The details of the optical control section 100 (optical control device) are described below.

The light source section 101 (including an intensity enhancement section and an irradiation section) included in the optical control section 100 emits white illumination light for which light within a specific wavelength band is enhanced (hereinafter may be referred to as "specific wavelength band-enhanced white light"). The specific wavelength band-enhanced white light emitted from the light source section 101 enters the thick end of the tapered rod 107 through the half mirror 102. The optical connector 108 is connected to the thin end of the tapered rod 107 so that the specific wavelength band-enhanced white light that has exited from the tapered rod 107 is transmitted to the illumination light input end of the optical fiber 201. The specific wavelength band-enhanced white light is applied to an observation target 10 as small spot light through the emitting end 203 of the optical fiber 201, and return light from the observation target 10 enters the emitting end 203 of the optical fiber 201. s The return light from the observation target 10 is transmitted through the optical fiber 201, enters the tapered rod 107 through the optical connector 108, is reflected by the half mirror 102, and enters the light detection section 103.

The return light that has entered the light detection section 103 is dispersed by a spectroscope 104 (prism or diffraction grating), and applied to an optical sensor 105 in which photoelectric conversion elements are arranged in a row along the direction in which the spectral light is dispersed (diffused). The optical sensor 105 is formed by arranging a plurality of line sensors formed by a photodiode or a phototransistor that implements photoelectric conversion, a plurality of photomultipliers, and the like. The photoelectric conversion elements are disposed so that one photoelectric conversion element corresponds to a given unit wavelength band (e.g., 10 nm) of the spectral light. The spectral light is sampled by the optical sensor 105 at specific wavelength intervals, and converted into an electrical signal. The electrical signal is output to the A/D conversion section 106 as analog spectral data.

The A/D conversion section 106 quantizes the sampled analog spectral data using a given number of bits (e.g., 16 bits) to obtain digital spectral data. The digital spectral data output from the A/D conversion section 106 is input to the image processing section 300.

The details of the light source section 101 according to the first embodiment are described below with reference to FIG. 2.

The light source section 101 includes white light sources 501 and 503, cut filters 502 and 504, filters 506 to 508, a total reflection mirror 509, a half mirror 510, and a condenser lens 511. The white light sources 501 and 503 are implemented by a halogen lamp, a xenon lamp, a white LED, or the like. The cut filters 502 and 504 are UV-IR cut filters that block light in the ultraviolet region and light in the infrared region contained in light emitted from the white light source. The filters 506 to 508 differ in spectral transmittance characteristics, and are provided in a folder 505 that can be moved automatically or manually.

Figure 2:
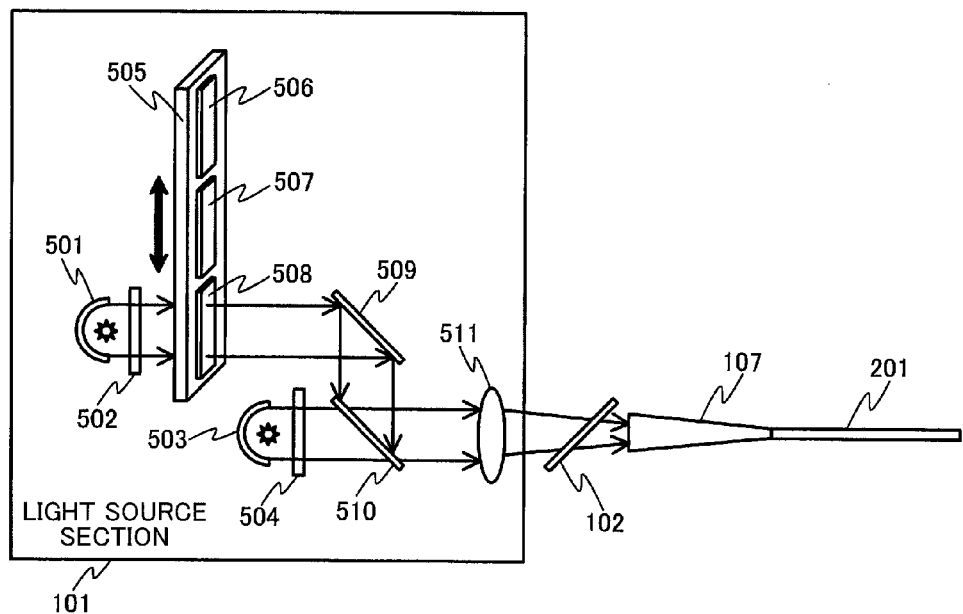
FIG. 2 illustrates a configuration example of a light source section.
Figure 3:
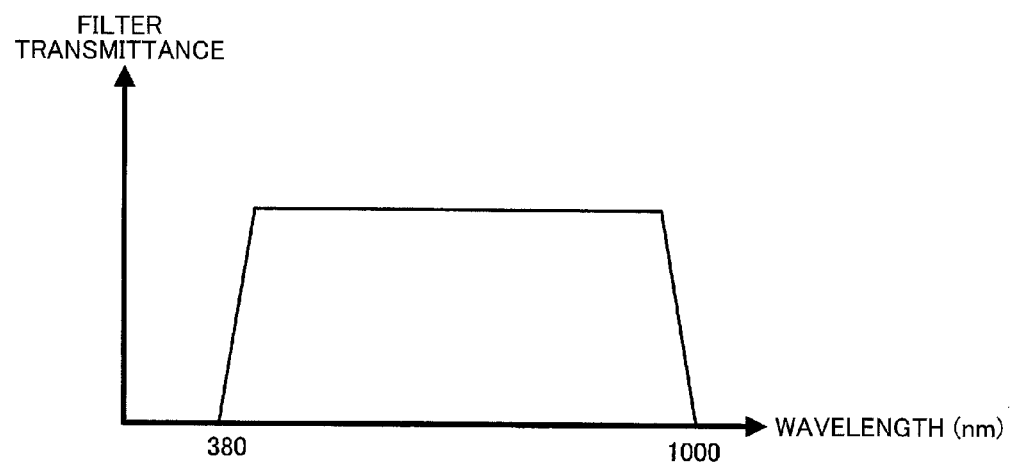
FIG. 3 illustrates the characteristics of a cut filter.
Figure 4:
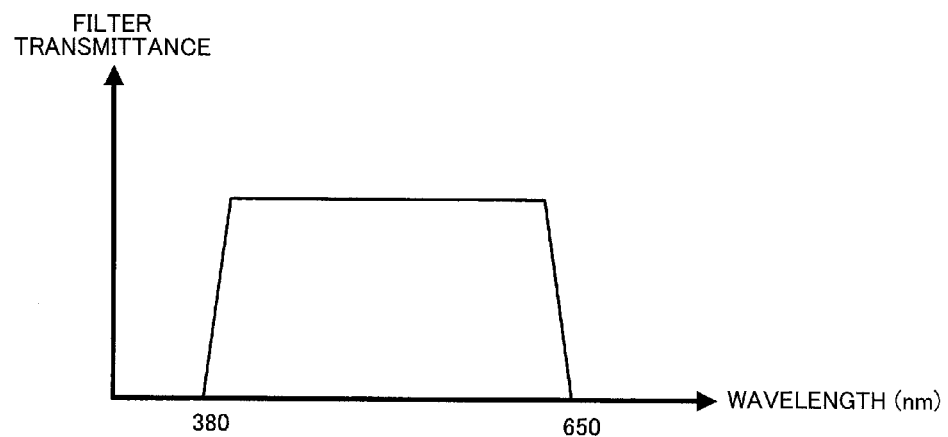
FIG. 4 illustrates the characteristics of a cut filter.

Parallel light (including approximately parallel light) is emitted from the white light sources 501 and 503, and the cut filters 502 and 504 having the filter transmittance illustrated in FIG. 3 or 4 block light within an unnecessary wavelength band to obtain white light. The filter transmittance illustrated in FIG. 3 and the filter transmittance illustrated in FIG. 4 differ as to whether or not to block light in the near infrared region. The filter transmittance illustrated in FIG. 4 is used when the scanning optical device (image processing device) has a mode in which fluorescence in the infrared region is observed, and the filter transmittance illustrated in FIG. 3 is used when the scanning optical device (image processing device) does not have a mode in which fluorescence in the infrared region is observed. The filters 502 and 504 may be provided in a turret (not illustrated in FIG. 2), and selectively used depending on the imaging mode. The details of the cut filter are described later.

The folder 505 can be moved so that the corresponding filter (506, 507, or 508) is automatically positioned in the optical path of the white light when the imaging mode has been designated by the control section 109.

The filter (508, 507, or 506) and the imaging mode (NBI mode, fluorescence imaging mode, or IRI mode) have a one-to-one relationship described below. Note that the filter 508 has the spectral transmittance characteristics illustrated in FIG. 5, the filter 507 has the spectral transmittance characteristics illustrated in FIG. 6, and the filter 506 has the spectral transmittance characteristics illustrated in FIG. 7.

Figure 5:
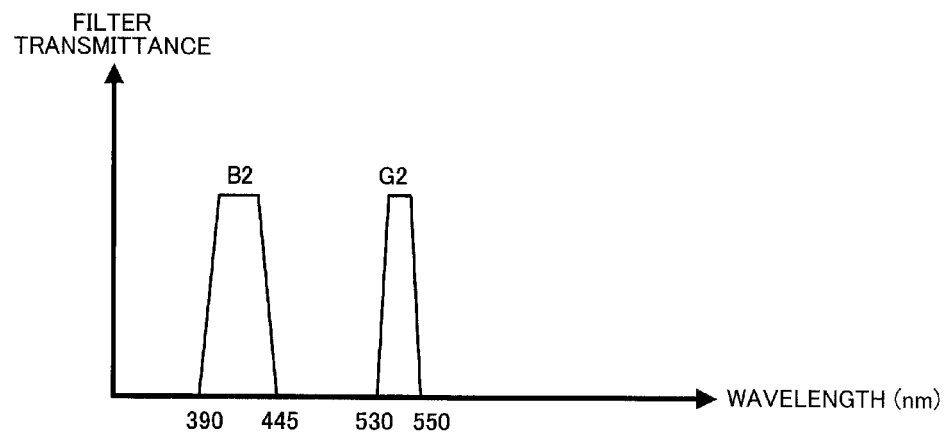
FIG. 5 illustrates the characteristics of an NBI mode filter.
Figure 6:
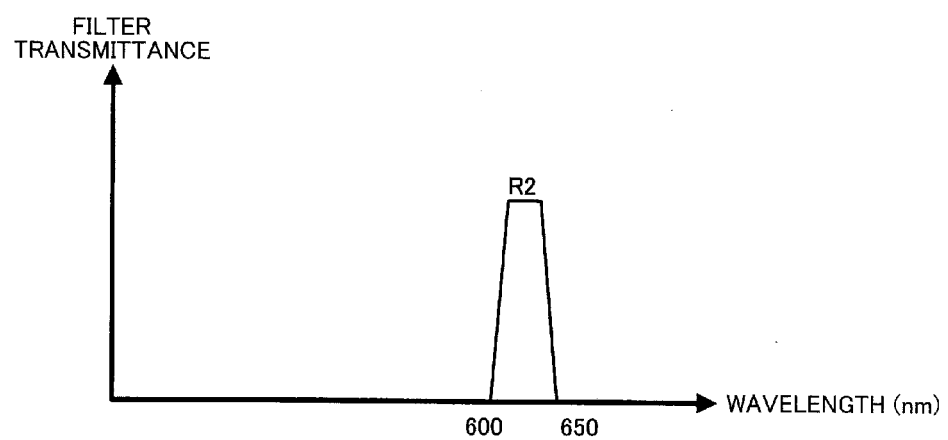
FIG. 6 illustrates the characteristics of a fluorescence imaging mode filter.
Figure 7:
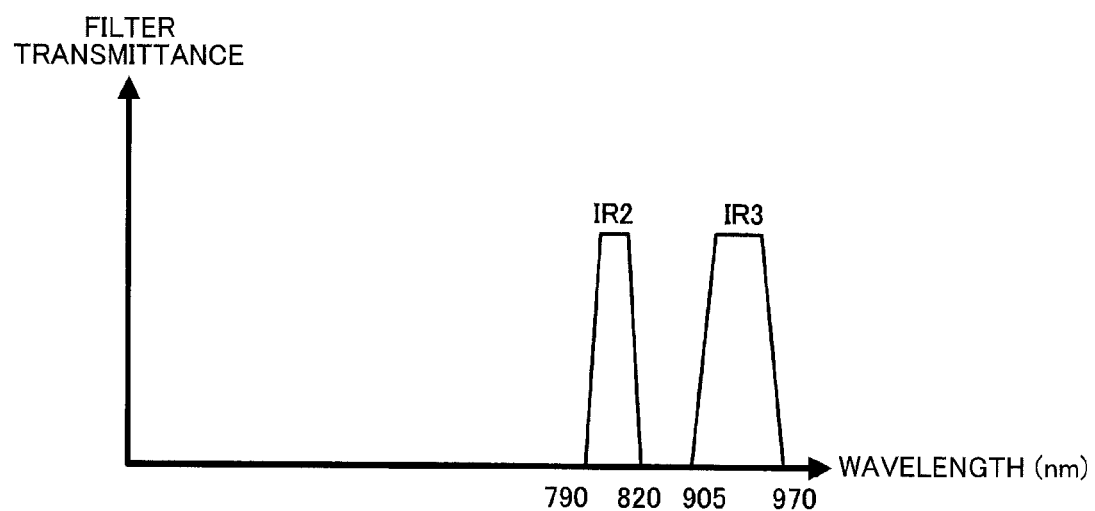
FIG. 7 illustrates the characteristics of an IRI mode filter.

The filter 508 having the spectral transmittance characteristics illustrated in FIG. 5 allows light within a wavelength band B2 (390 to 445 nm) and light within a wavelength band G2 (530 to 550 nm) to pass through, and blocks light within a wavelength band other than the wavelength band B2 and the wavelength band G2. The spectral transmittance characteristics illustrated in FIG. 5 are used in the NBI mode in which a blood vessel and a microstructure of a surface layer of a mucous membrane are observed using two reflected light images (see JP-A-2006-68113). The filter 507 having the spectral transmittance characteristics illustrated in FIG. 6 allows light within a wavelength band R2 (600 to 650 nm) to pass through, and blocks light within a wavelength band other than the wavelength band R2. The spectral transmittance characteristics illustrated in FIG. 6 are used in the fluorescence imaging mode in which fluorescence in the infrared region produced by a fluorescent agent is observed using light that has passed through the filter as excitation light, for example. The filter 506 having the spectral transmittance characteristics illustrated in FIG. 7 allows light within a wavelength band IR2 (790 to 820 nm) (near infrared region) and light within a wavelength band IR3 (905 to 970 nm) (near infrared region) to pass through, and blocks light within a wavelength band other than the wavelength band IR2 and the wavelength band IR3. The spectral transmittance characteristics illustrated in FIG. 7 are used in the IRI mode in which reflected light images due to light in the near infrared region that has passed through the filter are observed.

In the NBI mode, white light emitted from the white light source 501 from which light within an unnecessary wavelength band has been removed by the filter 502 having the filter transmittance characteristics illustrated in FIG. 3 passes through the filter 508 provided in the folder 505. Since the filter 508 has the transmittance characteristics illustrated in FIG. 5, special light that contains only light within the wavelength band B2 (390 to 445 nm) and light within the wavelength band G2 (530 to 550 mm) is obtained (see FIG. 8B). The special light is reflected by the total reflection mirror 509, and is incident on the half mirror 510. On the other hand, white light emitted from the white light source 503 from which light within an unnecessary wavelength band has been removed by the filter 504 having the filter transmittance characteristics illustrated in FIG. 3 (see FIG. 8A) is incident on the half mirror 510. The two types of light incident on the half mirror 510 form specific wavelength band-enhanced white light, which is incident on the condenser lens 511. The specific wavelength band-enhanced white light is narrowed by the condenser lens 511, and enters the thick end (end face) of the tapered rod 107 through the half mirror 102. The light source section 101 thus emits white light for which the specific wavelength band (B2 and G2 in the NBI mode) is enhanced (see FIG. 8C).

In the fluorescence imaging mode, the filters 502 and 504 have the characteristics illustrated in FIG. 4. Therefore, special light that contains only light within the wavelength R2 (600 to 650 nm) is obtained through the filter 507, and is incident on the half mirror 510. On the other hand, light that contains light within the wavelength band illustrated in FIG. 9A is obtained through the filter 504, and is incident on the half mirror 510. The light source section 101 thus emits white light having the spectral radiant characteristics illustrated in FIG. 9C.

In the IRI mode, the filters 502 and 504 have the characteristics illustrated in FIG. 3. Therefore, special light that contains only light within the wavelength IR2 (790 to 820 nm) and light within the wavelength IR3 (905 to 970 nm) (see FIG. 10B) is obtained through the filter 506, and is incident on the half mirror 510. On the other hand, light that contains light within the wavelength band illustrated in FIG. 10A is obtained through the filter 504, and is incident on the half mirror 510. The light source section 101 thus emits white light having the spectral radiant characteristics illustrated in FIG. 10C.

As described above, it is necessary to change the characteristics of the cut filters 502 and 504 between the case of using the filter 507 used in the fluorescence imaging mode and the case of using the filter 506 used in the IRI mode. The reasons therefor are described below with reference to FIGS. 11A to 11E and FIGS. 12A to 12D.

FIGS. 11A to 11E are views illustrating a problem that occurs when using the cut filters 502 and 504 having the characteristics illustrated in FIG. 3 while using the filter 507 used in the fluorescence imaging mode.

Figure 11A:
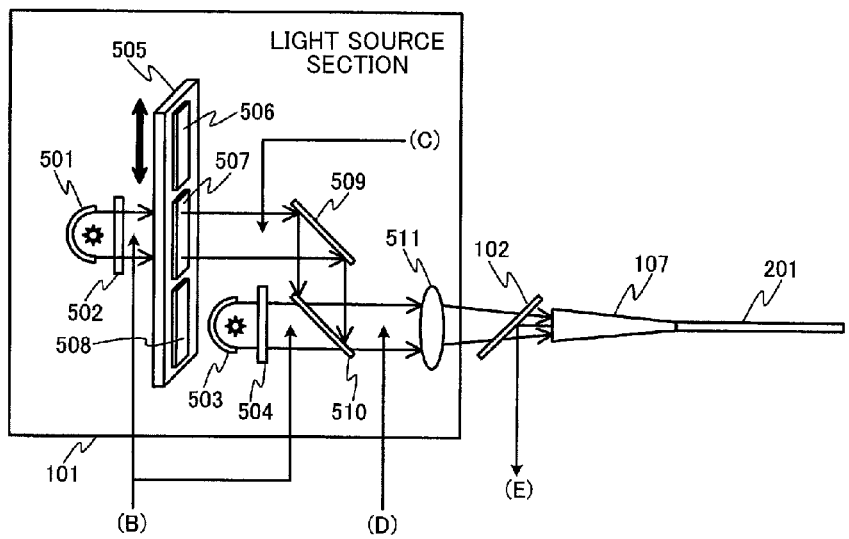
FIGS. 11A to 11E are views illustrating a problem that occurs when using an inappropriate cut filter in a fluorescence imaging mode.
Figure 11B:
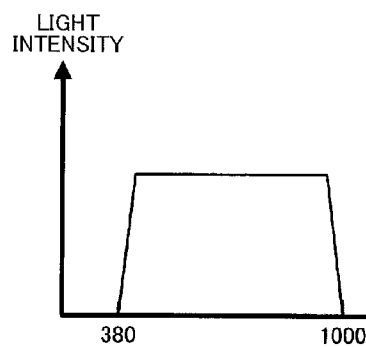
Figure 11C:
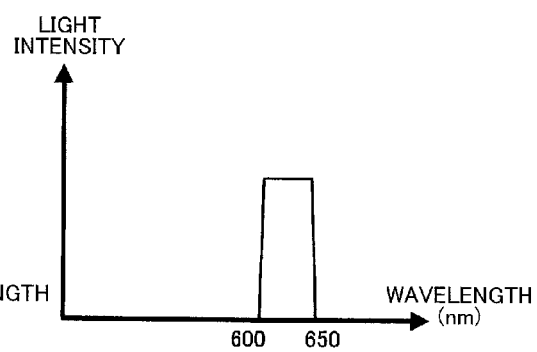
Figure 11D:
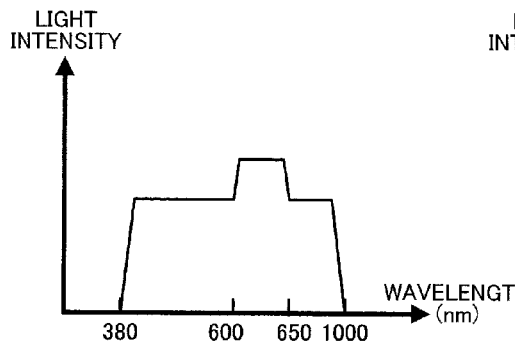
Figure 11E:
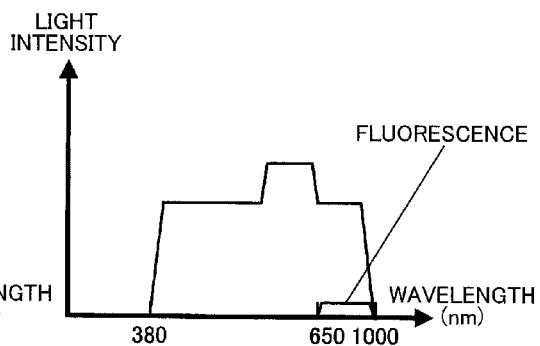

Light at a position B in FIG. 11A that has passed the cut filter 502 or 504 has the characteristics illustrated in FIG. 11B. Light at a position C in FIG. 11A that has passed the filter 507 used in the fluorescence imaging mode has the characteristics illustrated in FIG. 11C. Light at a position D in FIG. 11A that is obtained by synthesizing the light at the position B and the light at the position C has the characteristics illustrated in FIG. 11D. When the light having the characteristics illustrated in FIG. 11D is applied to the observation target, fluorescence within a wavelength band of 650 nm or more is produced due to excitation light within a wavelength band of 600 to 650 nm. However, since the intensity of the fluorescence is significantly lower than that of the reflected light of the illumination light, it is difficult to observe the fluorescence due to the reflected light (see FIG. 11E). Therefore, it is necessary to prevent a situation in which the wavelength band of the reflected light of the illumination light overlaps the wavelength band of the fluorescence when performing fluorescence imaging. Specifically, it is necessary to use the cut filters 502 and 504 having the characteristics illustrated in FIG. 4 instead of the characteristics illustrated in FIG. 3, and use the specific wavelength band-enhanced white light illustrated in FIG. 9C as the illumination light.

FIGS. 12A to 12D are views illustrating a problem that occurs when using the cut filters 502 and 504 having the characteristics illustrated in FIG. 4 while using the filter 506 used in the IRI mode.

Figure 12A:
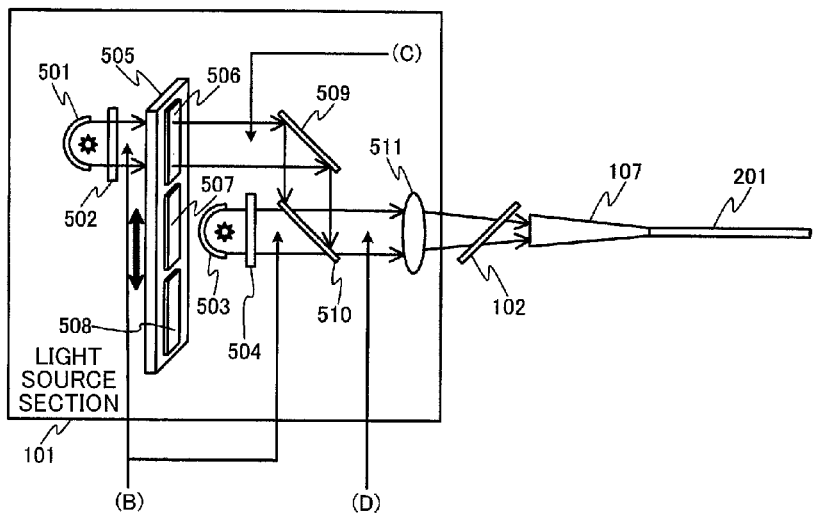
FIGS. 12A to 12D are views illustrating a problem that occurs when using an inappropriate cut filter in an IRI mode.
Figure 12B:
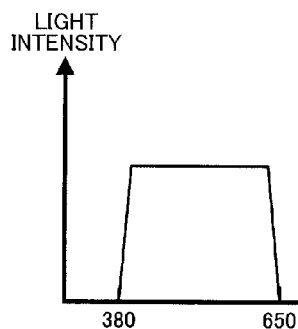
Figure 12C:
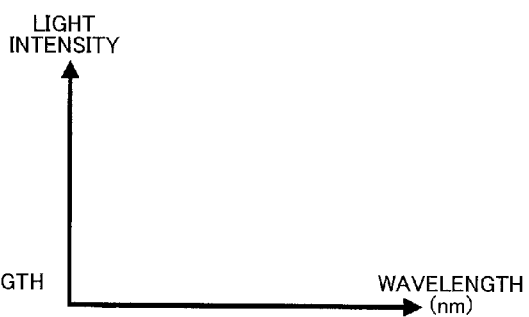
Figure 12D:
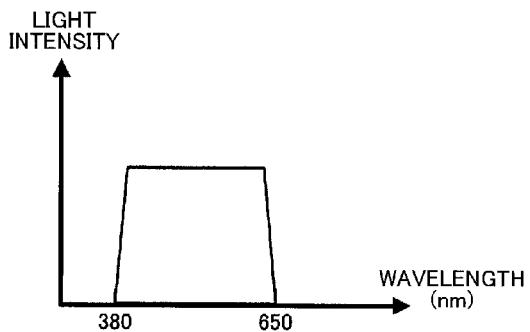

Light at a position B in FIG. 12A that has passed the cut filter 502 or 504 has the characteristics illustrated in FIG. 12B. Light at a position C in FIG. 12A that has passed the filter 506 used in the IRI mode has the characteristics illustrated in FIG. 12C. Light at a position D in FIG. 12A that is obtained by synthesizing the light at the position B and the light at the position C has the characteristics illustrated in FIG. 12D. As illustrated in FIG. 12C, light within a wavelength band of 380 to 650 nm is completely blocked by the filter 506. Therefore, specific wavelength band-enhanced white light cannot be acquired at the position D. Specifically, it is necessary to use the cut filters 502 and 504 having the characteristics illustrated in FIG. 3 instead of the characteristics illustrated in FIG. 4.

It is necessary to appropriately select the characteristics of the cut filters 502 and 504 depending on the mode for the above reasons. Note that the cut filters 502 and 504 may have the characteristics illustrated in FIG. 3 or 4 in the NBI mode, differing from the fluorescence imaging mode and the IRI mode.

The details of the insertion section 200 are described below.

Figure 20:
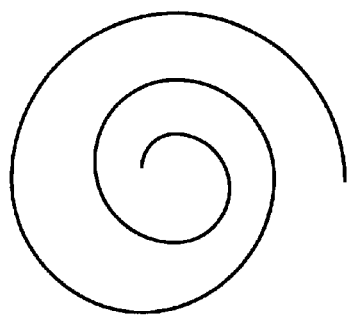
FIG. 20 illustrates an example of a spot light scan path according to one embodiment of the invention.

The insertion section 200 is connected to the optical connector 108. The specific wavelength band-enhanced white light emitted from the light source section 101 enters the optical fiber 201 through the tapered rod 107. The actuator 202 included in the insertion section 200 is disposed to concentrically cover the optical fiber 201. The actuator 202 vibrates at a given frequency in two axial directions that perpendicularly intersect the axis of the optical fiber 201, so that the part of the optical fiber 201 that is not covered with the actuator 202 and extends to the emitting end 203 resonates. The vibrations of the actuator 202 are controlled based on a control signal output from the control section 109. The control section 109 variably controls the vibration amplitude of the actuator 202 in the two axial directions so that the emitting end 203 cyclically and repeatedly draws a spiral path (see FIG. 20). Path position information that indicates the relationship between the control information about the actuator 202 and the position of the emitting end 203 along the spiral path is stored in the control section 109 as a table or a function.

The specific wavelength band-enhanced white light is applied to the observation target 10 as small spot light from the emitting end 203 that draws the spiral path. Return light due to the spot light corresponds to pixel information about the captured image. The return light enters the optical fiber 201 through the emitting end 203, passes through the tapered rod 107, is reflected by the half mirror 102, and enters the light detection section 103.

Although an example in which the return light enters the emitting end 203 has been described above, the emitting section may differ from the return light-receiving section. For example, return light-receiving fibers may be secured around an emitting fiber. This makes it possible to acquire more of the return light.

The details of the image processing section 300 are described below.

The return light that has entered the light detection section 103 is output to the classification section 301 as the digital spectral data. The classification section 301 receives the digital spectral data from the light detection section 103, and receives a spectral data weighting coefficient for each color signal that corresponds to the imaging mode from the control section 109. The classification section 301 (color signal generation section) multiplies the digital spectral data corresponding to each wavelength by a given weight corresponding to each color signal, and calculates the product sum of the weighted spectral data to generate the color signals. The color signals thus generated are output to the scan conversion section 302.

When the imaging mode is the NBI mode, for example, the classification section 301 generates an R signal, a G signal, a B signal, a G2 signal (NBI-G signal), and a B2 signal (NBI-B signal).

The scan conversion section 302 receives the color signals from the classification section 301, and receives the path position information about the emitting end 203 of the optical fiber 201 from the control section 109. The color signals input to the scan conversion section 302 are stored in a memory. A one-screen image in raster scan format for a normal display is generated by a conversion process based on the color signals (spiral color signals) corresponding to the one-screen path and the path position information. The pixel data may be absent at a given sampling position in raster scan format when merely rearranging the pixel data. In this case, the pixel (pixel data) is generated by performing an interpolation process using peripheral pixels. The scan conversion section 302 generates a one-screen image respectively using each color signal (e.g., R signal, G signal, B signal, G2 signal, and B2 signal). The color signals (e.g., R signal, G signal, and B signal) corresponding to the normal light image are output to the normal light image generation section 303, and the color signals (e.g., G2 signal and B2 signal) corresponding to the special light image are output to the special light image generation section 304.

The normal light image generation section 303 and the special light image generation section 304 perform image processing (e.g., noise reduction process, color correction process, grayscale transformation process, and enhancement process), and respectively output the normal light image and the special light image to the output image generation section 305.

The output image generation section 305 detects a brown area (i.e., a lesion area such as epidermoid cancer) from the special light image input from the special light image generation section 304. When the output image generation section 305 has determined that an area having a given hue has an area equal to or larger than a given value, the output image generation section 305 generates an output image in which the special light image is superimposed on the normal light image in that area. The output image generated by the output image generation section 305 is output to the display section 400.

The display section 400 (display) displays the output image input from the output image generation section 305.

The details of the classification section 301, the scan conversion section 302, and the output image generation section 305 are described below with reference to FIGS. 13 and 14.

Figure 13:
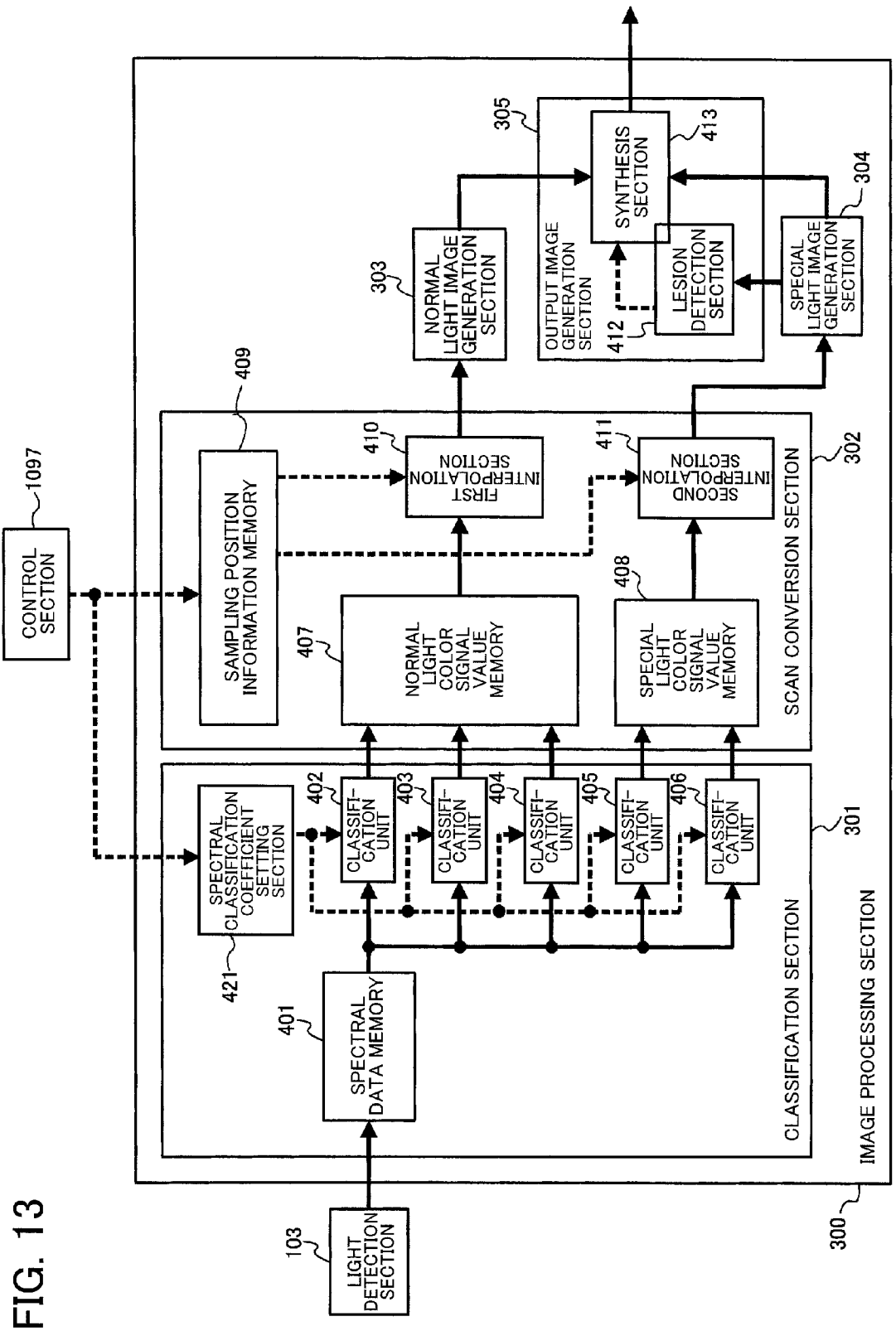
FIG. 13 illustrates a configuration example of an image processing section.

As illustrated in FIG. 13, the classification section 301 includes a spectral data memory 401, classification units 402 to 406, and a spectral classification coefficient setting section 421. Note that the configuration of the classification section 301 is not limited thereto. Various modifications may be made, such as omitting some of these elements.

The classification section 301 receives the digital spectral data from the light detection section 103, and temporarily stores the digital spectral data in the spectral data memory 401. The digital spectral data stored in the spectral data memory 401 includes sixty pieces of digital spectral data within a range of 400 to 1000 nm at intervals of 10 nm, for example. The sixty pieces of digital spectral data are output to the classification units 402 to 406.

The spectral classification coefficient setting section 421 receives sixty spectral data weighting coefficients corresponding to each color signal (R signal, G signal, B signal, B2 signal, and G2 signal in the NBI mode) that corresponds to the selected imaging mode from the control section 109, and inputs (sets) the corresponding weighting coefficient to the classification units 402 to 406 corresponding to each color signal.

Figure 14:
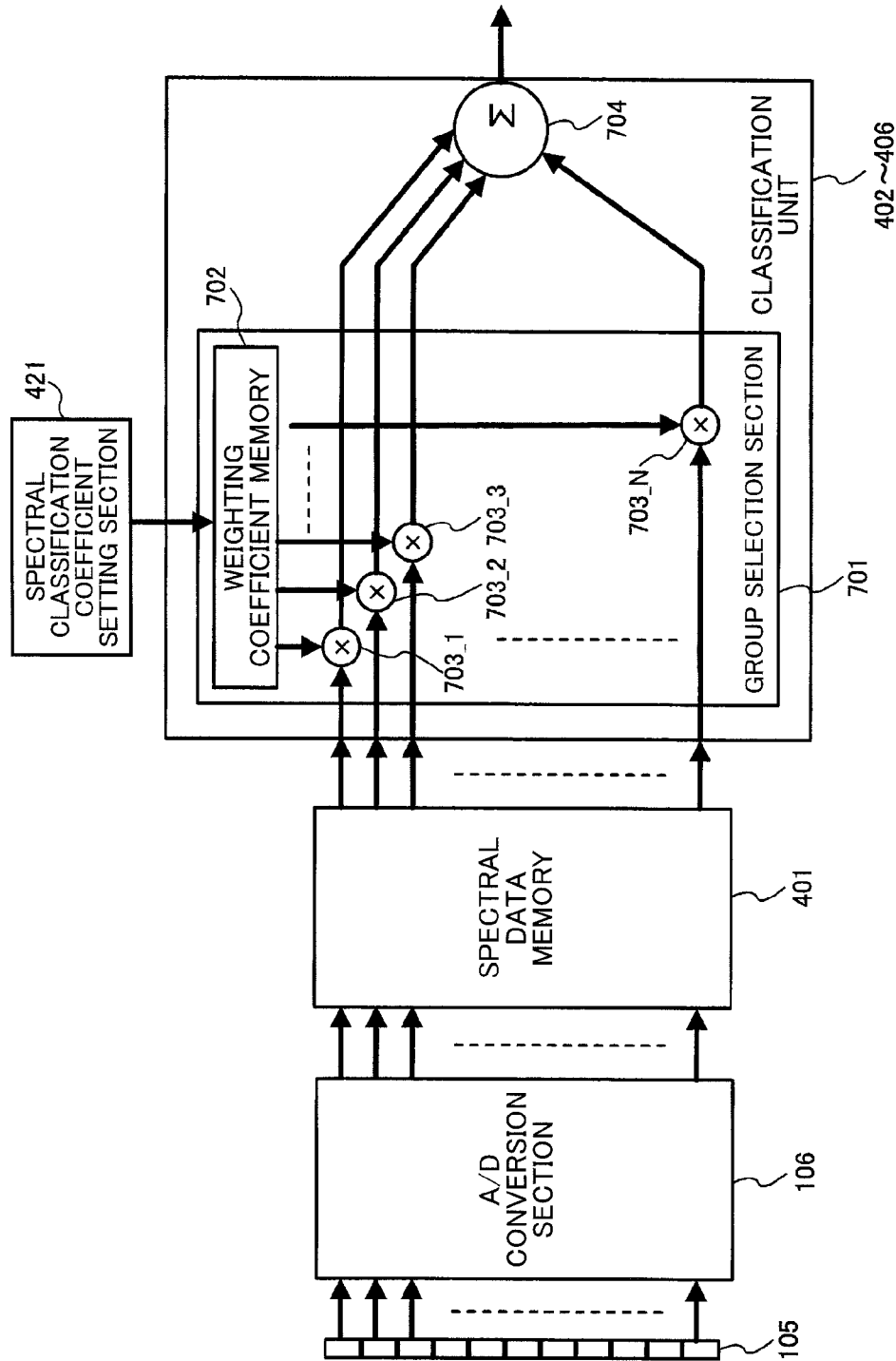
FIG. 14 illustrates a configuration example of a classification unit.

FIG. 14 illustrates a detailed configuration example of the classification units 402 to 406. The classification units 402 to 406 receive the weighting coefficient from the spectral classification coefficient setting section 421, and store the weighting coefficient in a weighting coefficient memory 702 illustrated in FIG. 14. Multipliers 703_1 to 703_N (N is 60 in this example) multiply the digital spectral data stored in the spectral data memory 401 by the weighting coefficient stored in the weighting coefficient memory 702, and an integrator 704 integrates the weighted spectral data to generate the color signal.

The weighting coefficient for the digital spectral data is described below.

In the NBI mode, the digital spectral data input to the classification units 402 to 406 is in a state in which the part corresponding to the specific wavelength band is enhanced (see FIG. 8C). The classification unit 402 generates the normal light R signal, the classification unit 403 generates the normal light G signal, and the classification unit 404 generates the normal light B signal. The classification unit 405 generates the special light B2 signal, and the classification unit 406 generates the special light G2 signal. Note that four classification units are used in the fluorescence imaging mode since only the R signal, the G signal, the B signal, and the R2 signal are used in the fluorescence imaging mode.

Figure 15:
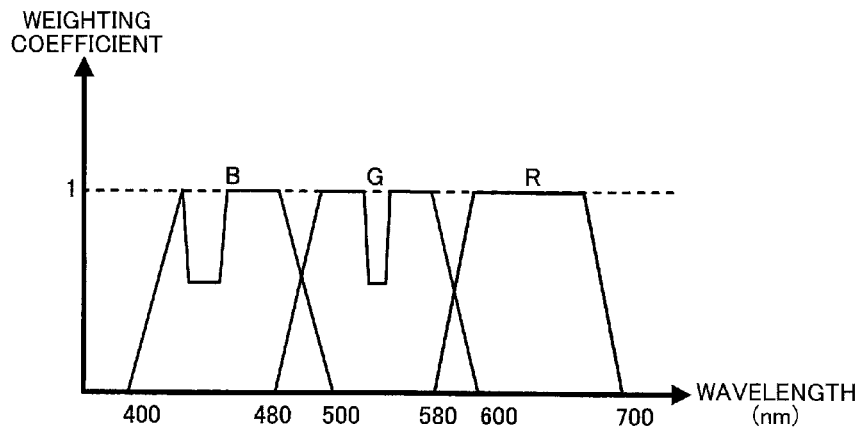
FIG. 15 is a view illustrating a weighting coefficient used in an NBI mode.
Figure 16:
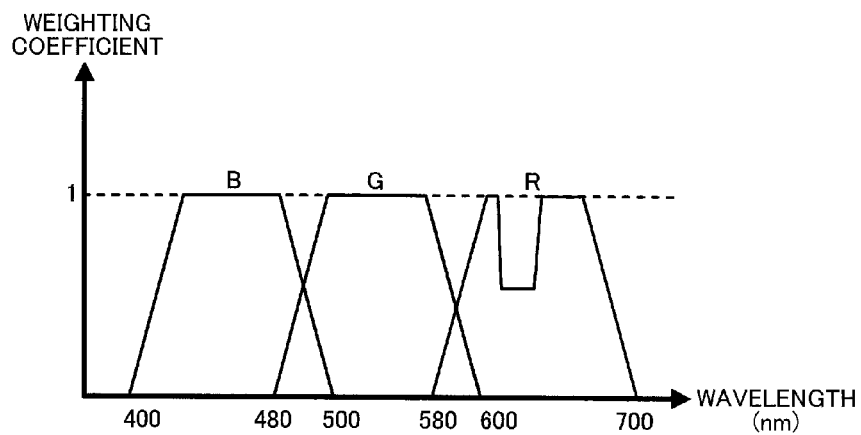
FIG. 16 is a view illustrating a weighting coefficient used in a fluorescence imaging mode.

It is necessary to correct the normal light R signal, the normal light G signal, and the normal light B signal so that the wavelength band (B2 and G2) enhanced for the special light is weighted in the same manner as the remaining wavelength band. Specifically, it is necessary to set the weighting coefficient input to the classification units 403 and 404 that respectively generate the G signal and the B signal so that the weighting coefficient in the enhanced wavelength band is reduced (see FIG. 15). In the fluorescence imaging mode, it is necessary to reduce the weighting coefficient in the wavelength band R2 (see FIG. 16). In the IRI mode, since the enhanced wavelength band (IR2 and IR3) does not overlap the wavelength band of the R signal, the G signal, and the B signal, it is unnecessary to reduce the weighting coefficient when generating the normal light signal.

The following description is given taking the NBI mode as an example unless otherwise specified. A person having ordinary skill in the art would readily appreciate that the process is similarly performed in the fluorescence imaging mode and the IRI mode.

The special light weighting coefficient has characteristics similar to the filter transmittance characteristics B2 or G2 illustrated in FIG. 5, and is set to the classification units 405 and 406 that respectively generate the B2 signal and the G2 signal.

Since the weighting coefficient can be set to "0" in an unnecessary wavelength region (see FIGS. 5 and 15), the digital spectral data can be partially and selectively used.

Figure 17:
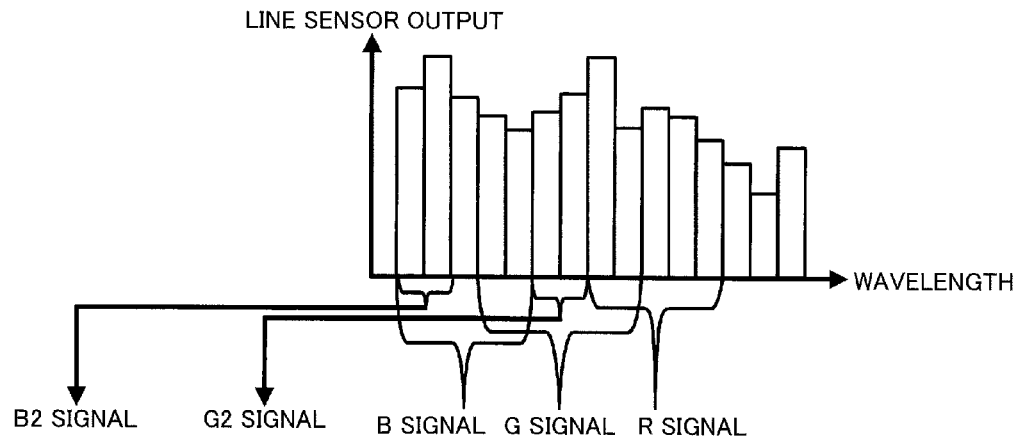
FIG. 17 is a view illustrating the relationship between an optical spectrum and each color signal in an NBI mode.
Figure 18:
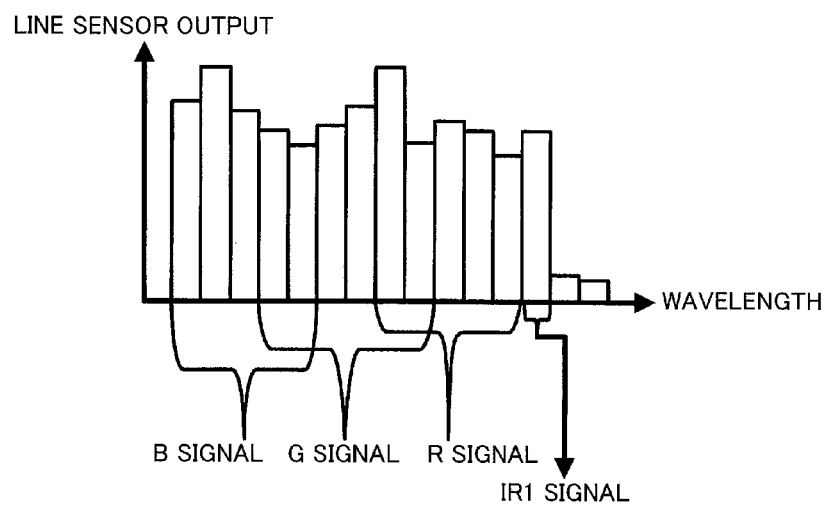
FIG. 18 is a view illustrating the relationship between an optical spectrum and each color signal in a fluorescence imaging mode.
Figure 19:
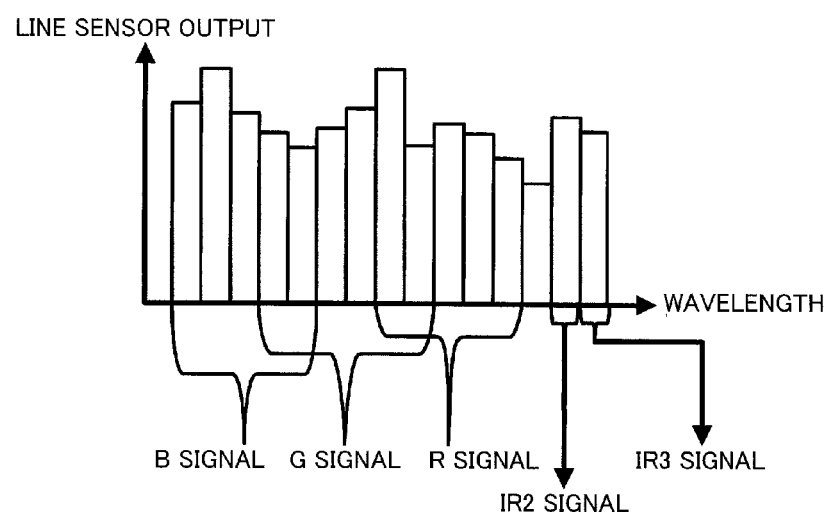
FIG. 19 is a view illustrating the relationship between an optical spectrum and each color signal in an IRI mode.

FIG. 17 schematically illustrates group classification of the digital spectral data used to generate five signals when the imaging mode is the NBI mode. In FIG. 17, the digital spectral data is divided into fifteen pieces of digital spectral data by 40 nm. The range of the digital spectral data used to generate each color signal is indicated in FIG. 17. FIG. 18 schematically illustrates group classification when the imaging mode is the fluorescence imaging mode, and FIG. 19 schematically illustrates group classification when the imaging mode is the IRI mode.

The scan conversion section 302 includes a normal light color signal value memory 407, a special light color signal value memory 408, a sampling position information memory 409, and interpolation sections 410 and 411.

The sampling position information memory 409 stores the path position information about the emitting end 203 of the optical fiber 201 that is input from the control section 109 in scan order. The path position information indicates two-dimensional coordinates.

The normal light color signal value memory 407 stores the R signal, the G signal, and the B signal input from the classification units 402, 403, and 404 in scan order.

The special light color signal value memory 408 stores the G2 signal and the B2 signal input from the classification units 405 and 406 in scan order.

The interpolation section 410 receives the R signal, the G signal, and the B signal from the normal light color signal value memory 407, and receives the path position information from the sampling position information memory 409. The interpolation section 410 stores the R signal, the G signal, and the B signal in a raster scan memory included in the interpolation section 410 based on the path position information. Since the R signal, the G signal, and the B signal indicate a two-dimensional spiral image (see FIG. 20), each pixel is displaced from the original position. The two-dimensional spiral scan format is converted into a raster scan format as described below, for example.

The pixel value of the raster scan sampling position is referred to as $R(x, y)$, and the pixel value of the two-dimensional spiral scan sampling position is referred to as $S(u, v)$. Note that x and u are coordinate values in the horizontal direction, and y and v are coordinate values in the vertical direction. The scale factor of the coordinates corresponds to the display magnification. Three two-dimensional spiral scan sampling positions $(u1, v1)$, $(u2, v2)$, and $(u3, v3)$ that surround the raster scan sampling position $(x, y)$ and are positioned at a short distance are searched. The distance D1 between the sampling position $(u1, v1)$ and the sampling position $(x, y)$, the distance D2 between the sampling position $(u2, v2)$ and the sampling position $(x, y)$, and the distance D3 between the sampling position $(u3, v3)$ and the sampling position $(x, y)$ are calculated, and the pixel value $R(x, y)$ is calculated by the following expression (1).

$$R(x,y)=S(u1,v1)\alpha+S(u2,v2)\beta+S(u3,v3)\gamma$$

$$\alpha=(D2+D3)/\{2(D1+D2+D3)\}$$

$$\beta=(D1+D3)/\{2(D1+D2+D3)\}$$

$$\gamma=(D1+D2)/\{2(D1+D2+D3)\} \quad (1)$$

When a missing pixel is present at the raster scan sampling position after performing the above process, the pixel value of the missing pixel is determined by performing a linear interpolation process on peripheral (adjacent) pixels, or utilizing a median value (median filter).

Figure 21:
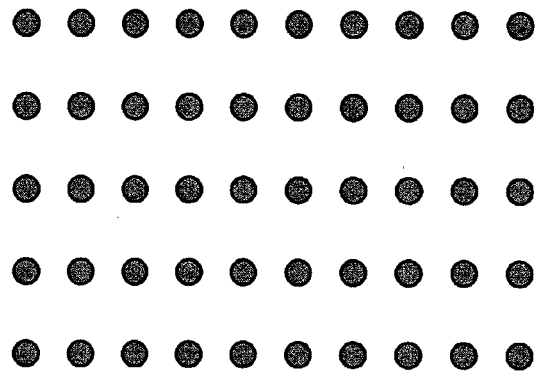
FIG. 21 is a view illustrating the configuration of a raster scan image.

A two-dimensional raster scan image (image in raster scan format) illustrated in FIG. 21 is obtained by the above interpolation process. The normal light image that has been subjected to scan conversion is output to the normal light image generation section 303.

The interpolation section 411 receives the G2 signal and the B2 signal from the special light color signal value memory 407, and receives the path position information from the sampling position information memory 409. The interpolation section 411 stores the G2 signal and the B2 signal in a raster scan memory included in the interpolation section 411 based on the path position information. The storage position is converted into raster scan format using the expression (1) in the same manner as in the case of processing the normal light image. The special light image that has been subjected to scan conversion is output to the special light image generation section 304. The special light image generation section 304 generates a pseudo 3-channel special light image using the two channels (G2 signal and B2 signal) input thereto, and outputs the special light image to a lesion detection section 412 and a synthesis section 413.

The output image generation section 305 includes the lesion detection section 412 and the synthesis section 413.

The lesion detection section 412 receives the special light image generated by the special light image generation section 304, and extracts an area having a given hue. The lesion position detection section 412 groups areas connected via the extracted area, and determines whether or not the area obtained by grouping is equal to or larger than a given threshold value. When the lesion position detection section 412 has determined that the area obtained by grouping is equal to or larger than the given threshold value, the lesion position detection section 412 sets a rectangular or circular area that encloses the area obtained by grouping, and outputs the rectangular or circular area to the synthesis section 413.

The synthesis section 413 receives a detected lesion area from the lesion detection section 412, receives the normal light image from the normal light image generation section 303, and receives the special light image from the special light image generation section 304. The synthesis section 413 removes part of the normal light image based on the detected lesion area, extracts the detected lesion area from the special light image at a position corresponding to the removed part of the normal light image, and adds the extracted area to the normal light image. The resulting image is output to the display section 400, and displayed on the display section 400.

The first embodiment may be applied to an optical control device that is provided in a scanning optical device (e.g., endoscope) that applies spot light to an observation target, and detects return light from the observation target while scanning with the spot light. The optical control device corresponds to the optical control section 100 according to the first embodiment, and includes an intensity enhancement section, an irradiation section, and the light detection section 103. The intensity enhancement section and the irradiation section are implemented by the light source section 101, for example. The intensity enhancement section acquires specific wavelength band-enhanced white light from the white light source, and the irradiation section applies the specific wavelength band-enhanced white light acquired by the intensity enhancement section. The light detection section 103 detects return light from the observation target when the specific wavelength band-enhanced white light is applied to the observation target.

Note that the term "spot light" used herein refers to light that is applied to the observation target in a spot-like shape. The term "specific wavelength band-enhanced white light" used herein refers to white light for which the intensity of light within a specific wavelength band (the wavelength band of excitation light that causes fluorescence to be produced, or the wavelength band of narrow-band light in a narrow sense) is enhanced as compared with the intensity of light within a wavelength band other than specific wavelength band. More specifically, the specific wavelength band-enhanced white light has characteristics as illustrated in FIG. 8C, 9C, or 10C.

According to the above configuration, since only the energy in the wavelength band of the special light can be increased while reducing the total energy, even if white light is concentrated as illumination light in a spot-like shape, the normal light image and the special light image can be simultaneously captured (acquired) while reducing damage to tissue to which light is applied. This makes it possible to emit bright illumination light that contains light within the wavelength band of the special light, and generate a clear special light image that is obtained by the reflected light and contains only a small amount of noise.

The intensity enhancement section may acquire the specific wavelength band-enhanced white light by increasing the intensity of light within the specific wavelength band.

This makes it possible to acquire the specific wavelength band-enhanced white light without using a white light source that emits white light having high intensity over the entire wavelength band. The expression "high intensity" refers to the degree of intensity when compared with a white light source used in connection with the third embodiment. In the third embodiment, the specific wavelength band-enhanced white light is acquired by blocking light within a wavelength band other than the specific wavelength band using a filter. Therefore, it is necessary to increase the intensity of light emitted from the white light source as compared with the first embodiment in order to acquire specific wavelength band-enhanced white light having an intensity equal to that obtained according to the first embodiment. The first embodiment is advantageous over the third embodiment as to this point.

The intensity enhancement section may acquire first white light and second white light from the white light source. The intensity enhancement section may acquire light within the specific wavelength band from the first white light, and may synthesize the light within the specific wavelength band and the second white light to acquire the specific wavelength band-enhanced white light.

According to the above configuration, since the light within the specific wavelength band can be acquired from the white light source by merely designing an arbitrary wavelength band filter, the specific wavelength band-enhanced white light can be acquired inexpensively.

A first white light source and a second white light source may be provided as the white light source. The intensity enhancement section may acquire the first white light from the first white light source, and may acquire the second white light from the second white light source. For example, the configuration illustrated in FIG. 2 may be employed.

According to the above configuration, when synthesizing the first white light and the second white light, specific wavelength band-enhanced white light having high intensity can be acquired by separately providing a white light source for acquiring the first white light and a white light source for acquiring the second white light.

The intensity enhancement section may acquire light within the specific wavelength band using a filter that allows light within the specific wavelength band to pass through (e.g., the filters 506, 507, and 508 illustrated in FIG. 2 (the filter characteristics are illustrated in FIGS. 5, 6, and 7)).

This makes it unnecessary to use a light source that emits the special light, and makes it possible to acquire the specific wavelength band-enhanced white light using only the white light source. This makes it possible to achieve a reduction in cost.

First to Nth filters (e.g., the filters 506, 507, and 508 illustrated in FIG. 2 (the filter characteristics are illustrated in FIGS. 5, 6, and 7)) may be provided as the filter, and the intensity enhancement section may acquire light within an ith specific wavelength band (e.g., 390 to 445 nm or 530 to 550 nm illustrated in FIG. 8B) using an ith filter among the first to Nth filters. More specifically, an NBI mode filter, a fluorescence imaging mode filter, and an IRI mode filter may be provided, and selectively used so that light within a different specific wavelength band is acquired.

This makes it possible to arbitrarily select the NBI mode, the fluorescence imaging mode, or the IRI mode by appropriately changing the filter.

The intensity enhancement section may apply a cut filter that blocks infrared light and ultraviolet light to the white light emitted from the white light source. A first cut filter and a second cut filter may be provided as the cut filter, and the first cut filter may have a high long-wavelength-side cut-off wavelength as compared with the second cut filter. For example, the first cut filter may have the characteristics illustrated in FIG. 3, and the second cut filter may have the characteristics illustrated in FIG. 4. Whether to apply the first cut filter or the second cut filter may be determined depending on the filter selected from the first to Nth filters. More specifically, the second cut filter is used when using the filter 507 used in the fluorescence imaging mode, and the first cut filter is used when using the filter 506 used in the IRI mode.

A problem occurs when the first cut filter (having the characteristics illustrated in FIG. 3) is used when using the filter 507 used in the fluorescence imaging mode, or the second cut filter (having the characteristics illustrated in FIG. 4) is used when using the filter 506 used in the IRI mode. The details of the problem have been described above with reference to FIGS. 11A to 11E and FIGS. 12A to 12D. In the fluorescence imaging mode, since the wavelength band of the reflected light overlaps the wavelength band of the fluorescence when using the first cut filter (see FIG. 11E), it is difficult to observe the fluorescence. In the IRI mode, it is impossible to acquire the specific wavelength band-enhanced white light when using the second cut filter (see FIG. 12D). Therefore, it is necessary to change the characteristics of the cut filter depending on the filter selected from the first to Nth filters.

It is possible to acquire white light having a wavelength band corresponding to the mode by appropriately selecting the characteristics of the cut filter.

The second cut filter may allow light within the specific wavelength band corresponding to the filter used to pass through, and may block light within a wavelength band corresponding to fluorescence produced by applying the light within the specific wavelength band. More specifically, when using the filter used in the fluorescence imaging mode, the second cut filter may allow light within a wavelength band of 600 to 650 nm corresponding to the specific wavelength band to pass through, and may block light within a wavelength band of 650 nm or more (light within a wavelength band longer than 650 nm) corresponding to fluorescence produced by applying light within a wavelength band of 600 to 650 nm, for example.

Specifically, the specific wavelength band-enhanced white light can be appropriately acquired as illumination light, but light within a wavelength band corresponding to fluorescence produced is not applied. This makes it possible to prevent a situation in which the wavelength band of the reflected light overlaps the wavelength band of the fluorescence (i.e., prevent a situation in which observation of the fluorescence is inhibited by the reflected light). Since the intensity of the fluorescence is significantly lower than that of the reflected light, it is difficult to observe the fluorescence when the wavelength band of the reflected light overlaps the wavelength band of the fluorescence.

The specific wavelength band may be narrower than the wavelength band of the white light. Specifically, the specific wavelength band may be the wavelength band of light absorbed by hemoglobin in blood. More specifically, the specific wavelength band may be 390 to 445 nm or 530 to 550 nm.

This makes it possible to implement narrow band imaging (NBI). NBI makes it possible to observe the structure of a surface area of tissue and a blood vessel located in a deep area. A lesion area (e.g., epidermoid cancer) that cannot be easily observed using normal light can be displayed as a brown area or the like by inputting the resulting signal to a given channel (R, G, or B), so that the lesion area can be reliably detected (i.e., a situation in which the lesion area is missed can be prevented). A wavelength band of 390 to 445 nm or 530 to 550 nm is selected from the viewpoint of absorption by hemoglobin and the ability to reach a surface area or a deep area of tissue. Note that the wavelength band is not limited thereto. For example, the lower limit of the wavelength band may decrease by about 5%, and the upper limit of the wavelength band may increase by about 5% depending on a variation factor (e.g., experimental results for absorption by hemoglobin and the ability to reach a surface area or a deep area of a living body).

The specific wavelength band may be the wavelength band of excitation light that causes a fluorescent substance to produce fluorescence.

This makes it possible to implement fluorescence imaging. Intrinsic fluorescence from a fluorescent substance (e.g., collagen) or fluorescence using a fluorescent agent can be observed by applying excitation light. In this case, the lesion area can be highlighted in a color differing from that of a normal mucous membrane, so that the lesion area can be reliably detected, for example.

The specific wavelength band may be the wavelength band of infrared light. Specifically, the specific wavelength band may be 790 to 820 nm or 905 to 970 nm.

This makes it possible to implement infrared imaging (IRI). Information about a blood vessel or a blood flow in a deep area of a mucous membrane that is difficult to observe visually, can be highlighted by intravenously injecting indocyanine green (ICG) (infrared marker) that easily absorbs infrared light, and applying infrared light within the above wavelength band, so that the depth of cancer invasion or the therapeutic strategy can be determined, for example. An infrared marker exhibits maximum absorption in a wavelength band of 790 to 820 nm, and exhibits minimum absorption in a wavelength band of 905 to 970 nm. Note that the wavelength band is not limited thereto. For example, the lower limit of the wavelength band may decrease by about 5%, and the upper limit of the wavelength band may increase by about 5% depending on a variation factor (e.g., experimental results for absorption by the infrared marker).

The scanning optical device according to the first embodiment may be a scanning endoscope.

This makes it possible to implement a scanning endoscope that includes the optical control device according to the first embodiment.

The first embodiment may also be applied to a control device that includes the optical control section 100 (optical control device) and the image processing section 300. The image processing section 300 generates a first image that corresponds to the white light, and a second image that corresponds light within the specific wavelength band, and generates an output image from the first image and the second image.

In this case, the optical control section acquires an optical signal, converts the optical signal into an electrical signal, and subjects the electrical signal to an A/D conversion process to acquire a digital signal. The image processing section performs image processing on the acquired digital signal. This makes it possible to display the image in an appropriate format. For example, a situation in which the color of the white light image changes as a resulting of enhancing light within the specific wavelength band is prevented, or a situation in which a lesion area is missed is prevented by changing the color of a given area (e.g., a lesion area observed during endoscopy).

The image processing section 300 may include the classification section 301 and the image generation section 306. The classification section 301 may classify optical signals included in the return light into a plurality of groups depending on the wavelength, and the image generation section 306 may generate an image of the observation target based on the optical signals that have been classified by the classification section and belong to the plurality of groups.

This makes it possible to classify the signals obtained from the return light into a plurality of groups depending on the characteristics of the image to be generated.

The classification section 301 may classify the optical signals into a first group that includes an optical signal that corresponds to the wavelength band of the white light and a second group that includes an optical signal that corresponds to the special light within the specific wavelength band.

This makes it possible to classify the optical signals into the first group corresponding to the white light and the second group corresponding to the special light. More specifically, the R signal, the G signal, and the B signal are classified into the first group (normal light group in a narrow sense), and the B2 signal and the G2 signal) are classified into the second group (special light group in a narrow sense) in the NBI mode. This makes it possible to appropriately generate the normal light image and the special light image.

The light detection section 103 may acquire an optical spectrum using the spectroscope 104. The classification section 301 may classify the optical signals into the first group and the second group based on the optical spectrum acquired by the light detection section 103.

This makes it possible to implement a system using a spectroscope that is a convenient optical device. For example, since the optical signals can be acquired at intervals of 10 nm using the spectroscope, it is unnecessary to use a special light source (e.g., a light source that emits light corresponding to the B2 signal of the narrow-band light), and the light source section can be formed by merely combining a normal white light source, a half mirror, a filter, and the like. Moreover, since the optical signals can be accurately acquired at equal intervals of 10 nm, for example, classification performed by the classification section 301 is facilitated.

The image generation section 306 may generate a first image based on the optical signals that belong to the first group, and may generate a second image based on the optical signals that belong to the second group. The first image (normal light image in a narrow sense) includes information within the wavelength band of the white light. The second image (special light image in a narrow sense) includes information within the wavelength band of the special light (e.g., the wavelength band of the narrow-band light B2 and the wavelength band of the narrow-band light G2).

This makes it possible to appropriately generate the normal light image and the special light image based on classification performed by the classification section 301.

The first group may include optical signals that respectively correspond to first to Pth wavelength bands that form the wavelength band of the white light. The image generation section 306 may generate first to Pth constituent images that form the first image based on the optical signals that respectively correspond to the first to Pth wavelength bands. The optical signals that respectively correspond to the first to Pth wavelength bands may be an R color optical signal, a G color optical signal, and a B color optical signal. The term "constituent image" used herein refers to each color image necessary for generating the normal light image. More specifically, the term "constituent image" used herein refers to an R image that includes an R signal over the entire image area, a G image that includes a G signal over the entire image area, and a B image that includes a B signal over the entire image area. The normal light image can be generated by inputting the R image to the R channel, inputting the G image to the G channel, and inputting the B image to the B channel.

This makes it possible to generate each color constituent image from each optical signal that corresponds to the wavelength band of the white light. For example, it is possible to acquire the R image from the R color optical signal, acquire the G image from the G color optical signal, and acquire the B image from the B color optical signal. The normal light image is generated from these constituent images. Although an example in which the R color optical signal, the G color optical signal, and the B color optical signal correspond to the wavelength band of the white light has been described above, the optical signals are not limited thereto.

The second group may include optical signals that respectively correspond to first to Qth (Q is an integer equal to or larger than 1) wavelength bands that form the specific wavelength band (e.g., the wavelength band B2 (390 to 445 nm) is the first wavelength band, and the wavelength band G2 (530 to 550 nm) is the second wavelength band in the NBI mode). The image generation section may generate first to Qth constituent images (e.g., a B2 image and a G2 image in the NBI mode) that form the second image based on the optical signals that respectively correspond to the first to Qth wavelength bands.

This makes it possible to generate each color constituent image from each optical signal that corresponds to the specific wavelength band. The special light image is generated from these constituent images. The constituent images may be based on optical signals that respectively correspond to the wavelength band B2 (narrow-band light) and the wavelength band G2 (narrow-band light), or may be based on optical signals that respectively correspond to the wavelength band IR2 and the wavelength band IR3 in the IRI mode. Note that the optical signals are not limited thereto.

The irradiation section may spirally apply the spot light. The image processing section 300 may include the scan conversion section 302 that acquires position information about the spot light, and the scan conversion section 302 may include the first interpolation section 410 and the second interpolation section 411. The first interpolation section 410 may convert the format of a first image signal that has been classified by the classification section 301 and corresponds to the first group into raster scan format based on the position information. Likewise, the second interpolation section 411 may convert the format of a second image signal that corresponds to the second group into raster scan format. The image generation section 300 may generate the first image based on the first image signal that has been converted into raster scan format, and may generate the second image based on the second image signal that has been converted into raster scan format.

This makes it possible to convert the format of the image (i.e., an unnatural image in which the observation target is distorted) obtained by a spiral scan into an image in raster scan format (see FIG. 21). Since a dead pixel without information may occur when merely converting the scan format, an interpolated value is calculated by a linear interpolation process, a median filter, or the like. An image can be generated based on the resulting raster scan image signal.

The first embodiment may also be applied to an optical scope that allows the white light applied by the irradiation section included in the optical control device according to the first embodiment to pass through, and transmits the return light from the observation target to the light detection section.

The term "optical scope" used herein corresponds to the insertion section 200 illustrated in FIG. 1. Specific examples of the optical scope include an upper gastrointestinal scope, a lower gastrointestinal scope, and the like. The optical scope according to the first embodiment can be reduced in diameter since a single section can be used as an illumination section and a light-receiving section.

The first embodiment may also be applied to a scanning optical device that includes an intensity enhancement section, an irradiation section, and a light detection section. The intensity enhancement section and the irradiation section are implemented by the light source section 101. The intensity enhancement section acquires specific wavelength band-enhanced white light from the white light source, and the irradiation section applies the specific wavelength band-enhanced white light acquired by the intensity enhancement section. The light detection section 103 detects return light from the observation target when the specific wavelength band-enhanced white light is applied to the observation target.

According to the above configuration, since only the energy in the wavelength band of the special light can be increased while reducing the total energy, even if white light is concentrated as illumination light in a spot-like shape, the normal light image and the special light image can be simultaneously captured (acquired) while reducing damage to tissue to which light is applied. This makes it possible to implement a scanning optical device (e.g., scanning endoscope in a narrow sense) that can emit bright illumination light that contains light within the wavelength band of the special light, and generate a clear special light image that is obtained by the reflected light and contains only a small amount of noise.

The scanning optical device may include a classification section.

This makes it possible to classify the optical signals obtained from the return light into a plurality of groups depending on the characteristics of the image to be generated.

Second Embodiment

Figure 22:
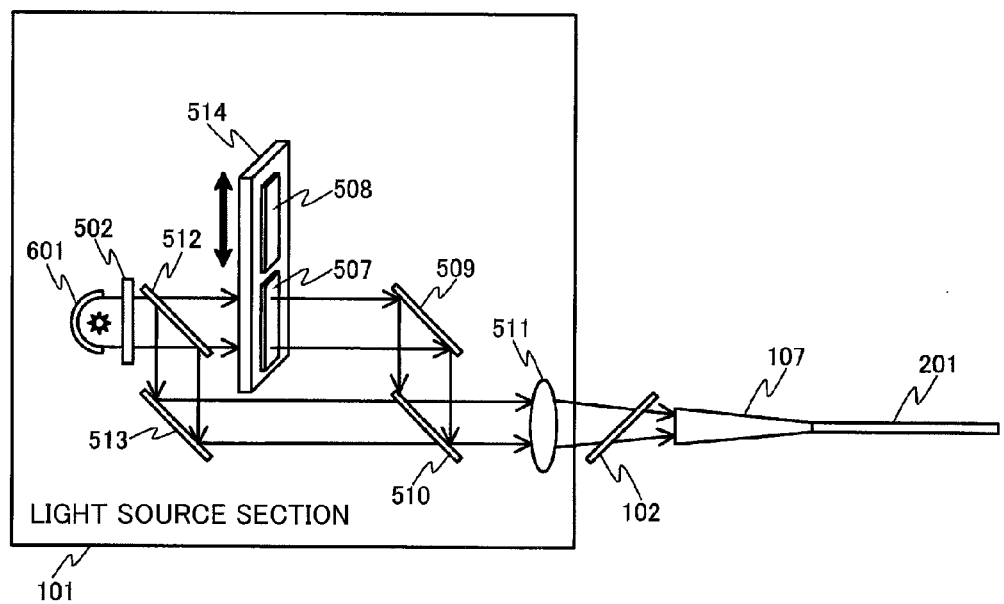
FIG. 22 illustrates another configuration example of a light source section.

The second embodiment is described below. Note that the configuration according to the second embodiment is identical with the configuration according to the first embodiment except for the light source section 101. Detailed description of the configuration identical with the configuration according to the first embodiment is omitted. FIG. 22 illustrates the configuration of the light source section 101 according to the second embodiment.

The light source section 101 includes a white light source 601 that emits light having an intensity higher than that of light emitted from the white light source according to the first embodiment, a UV-IR cut filter 502 that blocks light in the ultraviolet region and light in the infrared region contained in light emitted from the white light source, a folder 514 that accommodates filters (508 and 507) that differ in spectral transmittance characteristics and can be moved automatically or manually, total reflection mirrors 509 and 513, half mirrors 510 and 512, and a condenser lens 511.

Parallel light (including approximately parallel light) is emitted from the white light source 601, and the UV-IR cut filter 502 having the filter transmittance illustrated in FIG. 4 blocks light within an unnecessary wavelength band to obtain white light.

The folder 514 can be moved so that the corresponding filter (508 or 507) is automatically positioned in the optical path of the white light when the imaging mode has been designated by the control section 109.

The white light emitted from the white light source 601 from which light within an unnecessary wavelength band has been removed by the filter 502 passes through the half mirror 512, and enters the filter 507 or 508 provided in the folder 514. Light within the specific wavelength band is obtained through the filter. The light within the specific wavelength band is reflected by the total reflection mirror 509, and is incident on the half mirror 510. The white light reflected by the half mirror 512 is reflected by the total reflection mirror 513, and is incident on the half mirror 510. The two types of light incident on the half mirror 510 form specific wavelength band-enhanced white light, which is incident on the condenser lens 511. The specific wavelength band-enhanced white light is narrowed by the condenser lens 511, and enters the thick end (end face) of the tapered rod 107 through the half mirror 102.

The process is performed in the same manner as in the first embodiment after the specific wavelength band-enhanced white light has been obtained.

In the second embodiment, only the filters 508 and 507 (NBI mode and fluorescence imaging mode) are used since such a configuration makes it unnecessary to change (select) the characteristics of the cut filter 502. Three (or three or more) filters may be used in the same manner as in the first embodiment when changing (selecting) the characteristics of the cut filter 502.

According to the second embodiment, the single white light source 601 is provided as the white light source. The intensity enhancement section acquires first white light and second white light from the single white light source 601. For example, a half mirror may be used to acquire the first white light and the second white light from the single white light source 601. For example, the configuration illustrated in FIG. 22 may be employed. In FIG. 22, light that passes through the half mirror 512 (goes straight) corresponds to the first white light. The first white light passes through the filter (507 or 508) to obtain light within the specific wavelength band, which is reflected by the total reflection mirror 509. Light reflected by the half mirror 512 corresponds to the second white light. The second white light is reflected by the total reflection mirror 513.

The light source section can thus be formed using a single white light source. This makes it possible to simplify the configuration, and achieve a reduction in cost.

Third Embodiment

Figure 23:
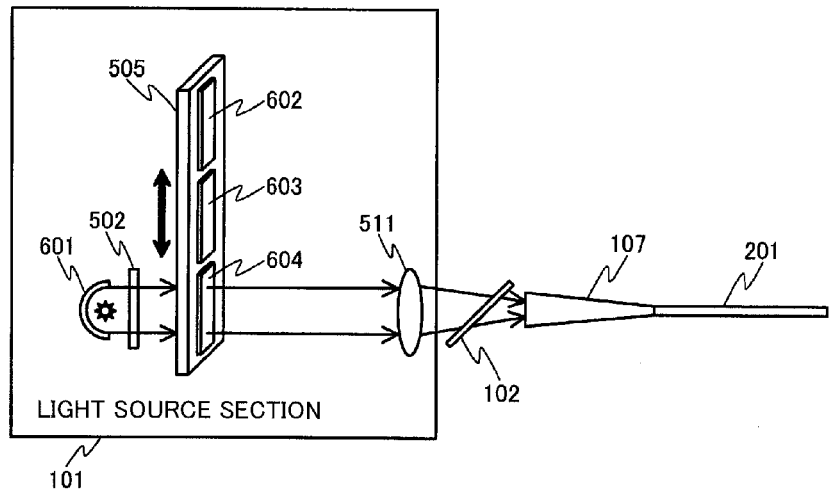
FIG. 23 illustrates another configuration example of a light source section.

The third embodiment is described below. Note that the configuration according to the third embodiment is identical with the configuration according to the first embodiment except for the light source section 101. Detailed description of the configuration identical with the configuration according to the first embodiment is omitted. FIG. 23 illustrates the configuration of the light source section 101 according to the third embodiment.

The light source section 101 includes a white light source 601 that emits light having an intensity higher than that of light emitted from the white light source according to the first embodiment, a UV-IR cut filter 502 that blocks light in the ultraviolet region and light in the infrared region contained in light emitted from the white light source, a folder 515 that accommodates filters (602, 603, and 604) that differ in spectral transmittance characteristics and can be moved automatically or manually, and a condenser lens 511.

Approximately parallel light is emitted from the white light source 601, and the UV-IR cut filter 502 having the filter transmittance illustrated in FIG. 3 blocks light within an unnecessary wavelength band to obtain white light.

The folder 505 can be moved so that the corresponding filter (602, 603, or 604) is automatically positioned in the optical path of the white light when the imaging mode has been designated by the control section 109.

Figure 27A:
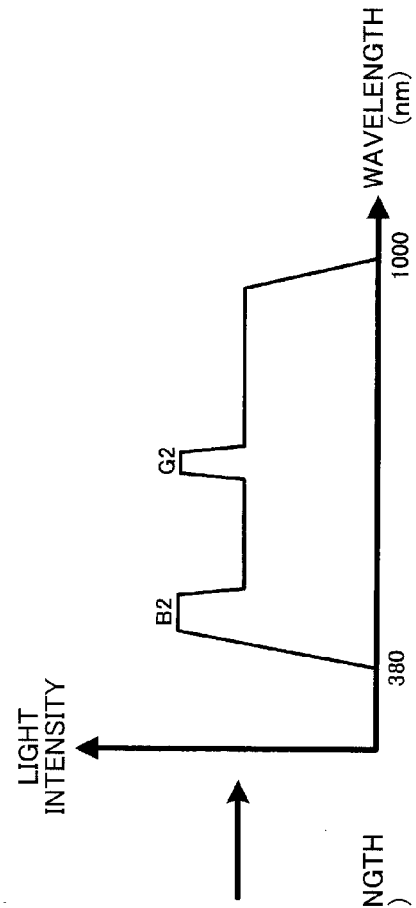
FIGS. 27A and 27B are views illustrating a specific wavelength band-enhanced white light acquisition method in an NBI mode.
Figure 27B:
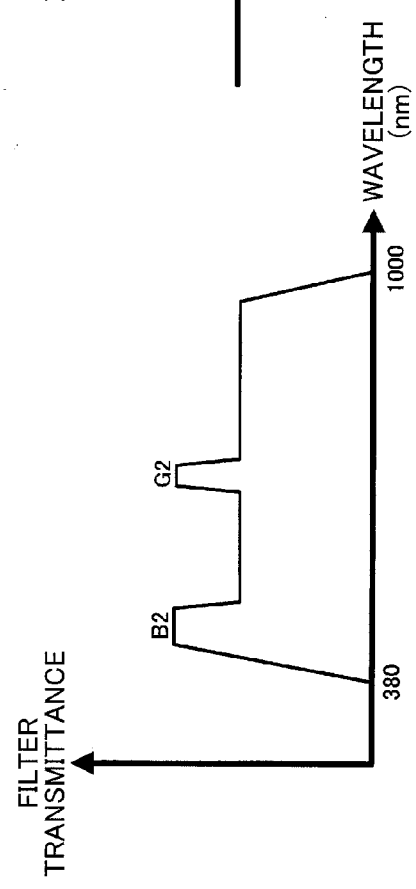
Figure 28A:
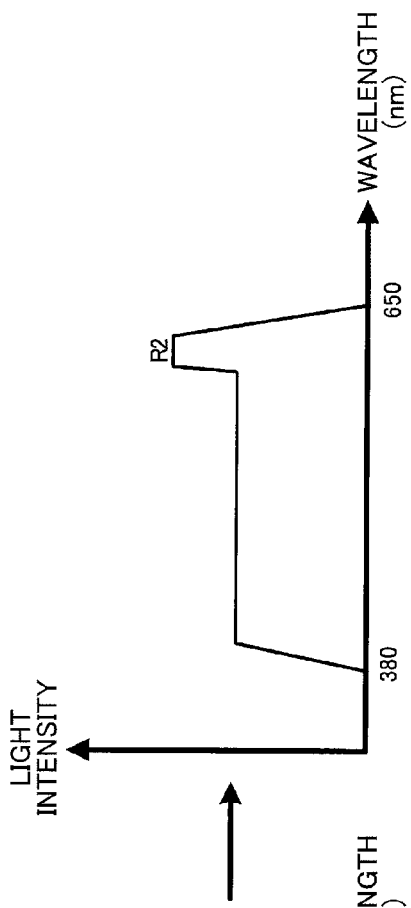
FIGS. 28A and 28B are views illustrating a specific wavelength band-enhanced white light acquisition method in a fluorescence imaging mode.
Figure 28B:
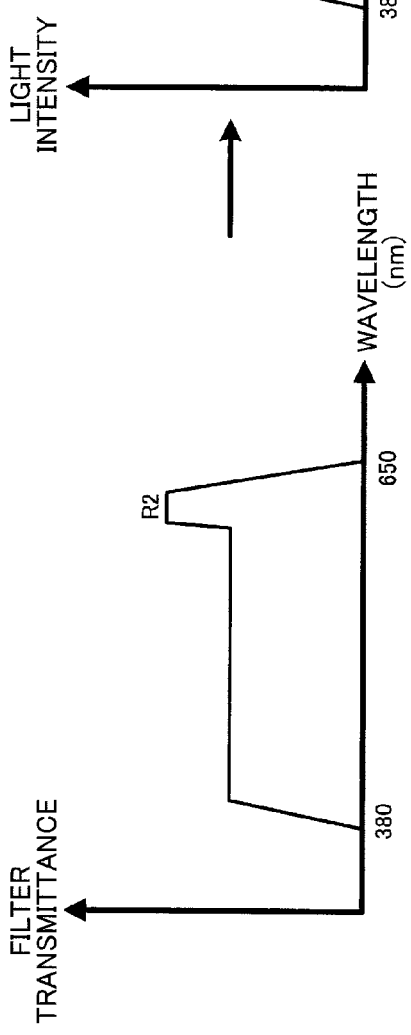

The white light (having the characteristic illustrated in FIG. 3) emitted from the white light source 601 from which light within an unnecessary wavelength band has been removed by the filter 502, enters the filter 602, 603, or 604 provided in the folder 505. The filter 602 has the characteristics illustrated in FIG. 24 (FIG. 27A). Therefore, white light in which the intensity of light within the wavelength bands G2 and B2 is high, and the intensity of light within a wavelength other than the wavelength bands G2 and B2 is reduced (see FIG. 27B), is obtained through the filter 602. The filter 603 has the characteristics illustrated in FIG. 25 (FIG. 28A). Therefore, white light in which the intensity of light within the wavelength band R2 is high, and the intensity of light within a wavelength other than the wavelength band R2 is reduced (see FIG. 28B), is obtained through the filter 603. The filter 604 has the characteristics illustrated in FIG. 26 (FIG. 29A). Therefore, white light in which the intensity of light within the wavelength bands IR2 and IR3 is high, and the intensity of light within a wavelength other than the wavelength bands IR2 and IR3 is reduced (see FIG. 29B), is obtained through the filter 604.

The resulting white light is incident on the condenser lens 511. The white light is narrowed by the condenser lens 511, and enters the thick end (end face) of the tapered rod 107 through the half mirror 102.

The process is performed in the same manner as in the first embodiment after the specific wavelength band-enhanced white light has been obtained.

According to the third embodiment, the intensity enhancement section acquires the specific wavelength band-enhanced white light by reducing the intensity of light within a wavelength band other than the specific wavelength band.

According to the above configuration, since it is unnecessary to synthesize (combine) two or more types of light, the configuration of the light source section can be simplified, and a reduction in cost can be achieved.

Figure 24:
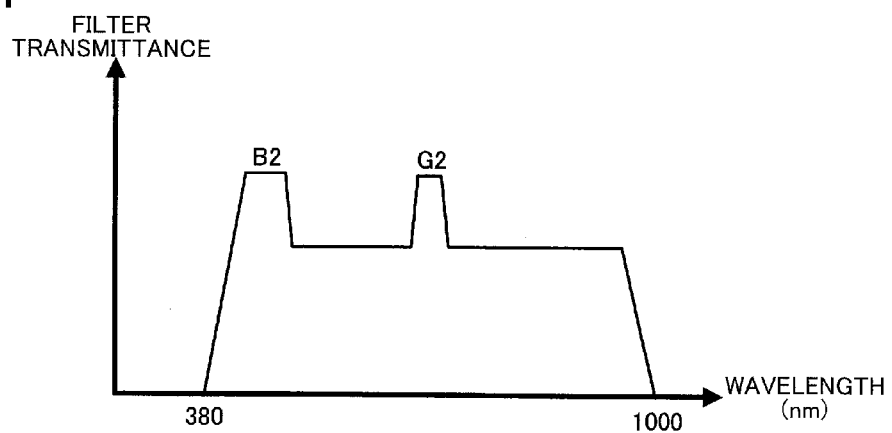
FIG. 24 illustrates the characteristics of an NBI mode filter.
Figure 25:
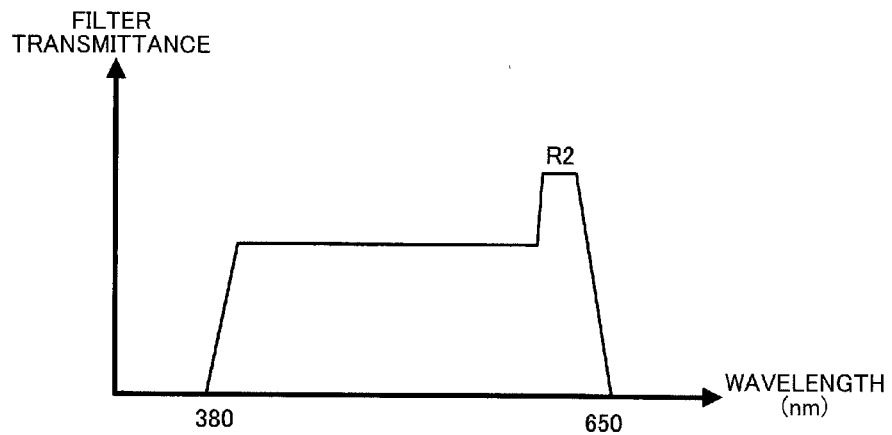
FIG. 25 illustrates the characteristics of a fluorescence imaging mode filter.
Figure 26:
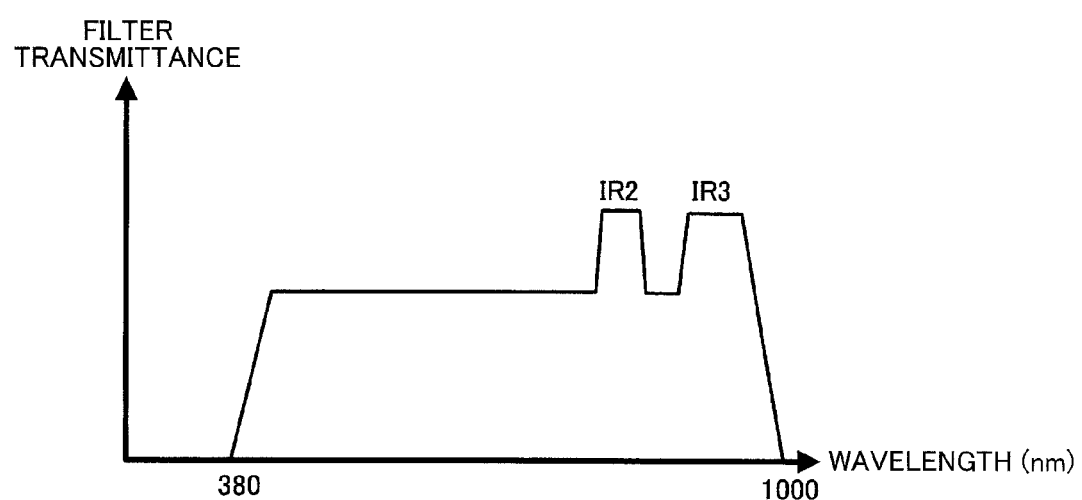
FIG. 26 illustrates the characteristics of an IRI mode filter.

The intensity enhancement section may acquire the specific wavelength band-enhanced white light using a filter that allows light within the specific wavelength band to pass through (e.g., the filters 602, 603, and 604 illustrated in FIG. 23 (the filter characteristics are illustrated in FIGS. 24, 25, and 26)).

This makes it unnecessary to use a light source that emits the special light, and makes it possible to acquire the specific wavelength band-enhanced white light using only the white light source. Since the specific wavelength band-enhanced white light can be acquired by applying only one filter, it is unnecessary to provide a plurality of light sources, a plurality of half mirrors, and the like, so that a reduction in cost can be achieved.

First to Mth filters (e.g., the filters 602 to 604 illustrated in FIG. 23 (the filter characteristics are illustrated in FIGS. 24 to 26)) may be provided as the filter, and the intensity enhancement section may acquire jth specific wavelength band-enhanced white light (e.g., light having the characteristic illustrated in FIG. 27B in the NBI mode) using a jth filter among the first to Mth filters. More specifically, an NBI mode filter, a fluorescence imaging mode filter, and an IRI mode filter may be provided, and selectively used so that different specific wavelength band-enhanced white light is acquired.

This makes it possible to arbitrarily select the NBI mode, the fluorescence imaging mode, or the IRI mode by appropriately changing the filter. Since the light source section can be formed using a single white light source, a reduction in cost can be achieved. Moreover, it is unnecessary to change (select) the characteristics of the cut filter 502.

The first to third embodiments according to the invention and the modifications thereof have been described above. Note that the invention is not limited to the first and to third embodiments and the modifications thereof. Various modifications and variations may be made without departing from the scope of the invention. A plurality of elements described in connection with the first to third embodiments and the modifications thereof may be appropriately combined to achieve various configurations. For example, an arbitrary element may be omitted from the elements described in connection with the first to third embodiments and the modifications thereof. The elements described in connection with different embodiments or modifications thereof may be appropriately combined. Specifically, various modifications and applications are possible without materially departing from the novel teachings and advantages of the invention.

Any term (e.g., normal light image and special light image) cited with a different term (e.g., first image and second image) having a broader meaning or the same meaning at least once in the specification and the drawings may be replaced by the different term in any place in the specification and the drawings.

Although only some embodiments of the present invention have been described in detail above, those skilled in the art will readily appreciate that many modifications are possible in the embodiments without materially departing from the novel teachings and advantages of this invention. Accordingly, all such modifications are intended to be included within scope of this invention.

What is claimed is:
1. A scanning endoscope comprising:
an optical control section that applies light emitted from a light source to an observation target as spot light that is applied in a spot-like shape, and detects reflected light from the observation target while scanning with the spot light; and
an image processing section that generates a first image that corresponds to white light and a second image that corresponds light within a specific wavelength band based on the reflected light detected by the optical control section;
the optical control section comprising:
an intensity enhancement section that enhances intensity of the light within the specific wavelength band that corresponds to the second image and is included in a wavelength band of white light emitted from a white light source;
an irradiation section that applies specific wavelength band-enhanced white light to the observation target, the specific wavelength band-enhanced white light being white light for which intensity of light within the specific wavelength band is enhanced by the intensity enhancement section; and
a light detection section that detects the reflected light from the observation target when the irradiation sec- tion applies the specific wavelength band-enhanced white light to the observation target, and generates spectral data, and the image processing section generates the second image based on the spectral data that corresponds to the specific wavelength band for which the intensity of light is enhanced, and generates the first image based on weighted spectral data calculated from the spectral data that corresponds to the specific wavelength band for which the intensity of light is enhanced and the spectral data that corresponds to a wavelength band other than the specific wavelength band while setting a weight applied to the spectral data that corresponds to the specific wavelength band to be smaller than a weight applied to the spectral data that corresponds to a wavelength band other than the specific wavelength band.

2. The scanning endoscope as defined in claim 1,
the intensity enhancement section acquiring the specific wavelength band-enhanced white light by increasing intensity of light within the specific wavelength band included in the wavelength band of the white light emitted from the white light source.

3. The scanning endoscope as defined in claim 2,
the intensity enhancement section acquiring first white light and second white light from the white light source, acquiring light within the specific wavelength band from the first white light, and synthesizing the light within the specific wavelength band and the second white light to acquire the specific wavelength band-enhanced white light.

4. The scanning endoscope as defined in claim 3,
a first white light source and a second white light source being provided as the white light source, and
the intensity enhancement section acquiring the first white light from the first white light source, and acquiring the second white light from the second white light source.

5. The scanning endoscope as defined in claim 3,
a single white light source being provided as the white light source, and
the intensity enhancement section acquiring the first white light and the second white light from the single white light source.

6. The scanning endoscope as defined in claim 3,
the intensity enhancement section acquiring the light within the specific wavelength band using a filter that allows light within the specific wavelength band to pass through.

7. The scanning endoscope as defined in claim 6,
first to Nth (N is an integer equal to or larger than 2) filters being provided as the filter, and
the intensity enhancement section acquiring light within an ith ($1 \le i \le N$) specific wavelength band as the light within the specific wavelength band using an ith filter among the first to Nth filters.

8. The scanning endoscope as defined in claim 1,
the intensity enhancement section acquiring the specific wavelength band-enhanced white light by reducing intensity of light within a wavelength band of white light other than the specific wavelength band, intensity of the white light having been enhanced over an entire wavelength band.

9. The scanning endoscope as defined in claim 8,
the intensity enhancement section reducing intensity of light within the wavelength band other than the specific wavelength band using a filter that attenuates light within the wavelength band other than the specific wavelength band included in the wavelength band of the white light.

10. The scanning endoscope as defined in claim 9,
first to Mth (M is an integer equal to or larger than 2) filters being provided as the filter, and
the intensity enhancement section acquiring jth ($1 \le j \le M$) specific wavelength band-enhanced white light as the specific wavelength band-enhanced white light using a jth filter among the first to Mth filters that attenuates light within the wavelength band other than the specific wavelength band.

11. The scanning endoscope as defined in claim 1,
the specific wavelength band being narrower than a wavelength band of the white light.

12. The scanning endoscope as defined in claim 1,
the specific wavelength band being a wavelength band of light absorbed by hemoglobin in blood.

13. The scanning endoscope as defined in claim 12,
the specific wavelength band being 390 to 445 nm or 530 to 550 nm.

14. The scanning endoscope as defined in claim 1,
the specific wavelength band being a wavelength band of infrared light.

15. The scanning endoscope as defined in claim 14,
the specific wavelength band being 790 to 820 nm or 905 to 970 nm.

16. The scanning endoscope as defined in claim 1,
the image processing section comprising:
    a classification section that classifies optical signals included in the detected reflected light into a plurality of groups depending on a wavelength that corresponds to each optical signal of the optical signals; and
    an image generation section that generates an image of the observation target based on an optical signal that belong to a group among the plurality of groups into which the optical signals have been classified by the classification section.

17. The scanning endoscope as defined in claim 16,
the classification section classifying the optical signals into at least a first group and a second group, the first group including an optical signal that corresponds to a wavelength band of the white light, and the second group including an optical signal that corresponds to special light within the specific wavelength band.

18. The scanning endoscope as defined in claim 17,
the light detection section acquiring an optical spectrum using a spectroscope, and
the classification section classifying the optical signals into the first group and the second group based on the optical spectrum acquired by the light detection section.

19. The scanning endoscope as defined in claim 17,
the image generation section generating the first image based on the optical signals that belong to the first group, and generating the second image based on the optical signals that belong to the second group, the first image including information within the wavelength band of the white light, and the second image including information within a wavelength band of the special light.

20. The scanning endoscope as defined in claim 19,
the first group including optical signals that respectively correspond to first to Pth (P is an integer equal to or larger than 2) wavelength bands that form the wavelength band of the white light, and the image generation section generating first to Pth constituent images that form the first image based on the optical signals that respectively correspond to the first to Pth wavelength bands.

21. The scanning endoscope as defined in claim 20,
the optical signals that respectively correspond to the first to Pth wavelength bands being an R color optical signal, a G color optical signal, and a B color optical signal.

22. The scanning endoscope as defined in claim 19,
the second group including optical signals that respectively correspond to first to Qth (Q is an integer equal to or larger than 1) wavelength bands that form the specific wavelength band, and
the image generation section generating first to Qth constituent images that form the second image based on the optical signals that respectively correspond to the first to Qth wavelength bands.

23. The scanning endoscope as defined in claim 17,
the irradiation section spirally applying the spot light to the observation target,
the image generation section including a scan conversion section that acquires position information about the spot light,
the scan conversion section including a first interpolation section and a second interpolation section,
the first interpolation section converting a format of a first image signal that corresponds to the first group into a raster scan format based on the position information about the spot light,
the second interpolation section converting a format of a second image signal that corresponds to the second group into a raster scan format based on the position information about the spot light, and
the image generation section generating the first image based on the first image signal that has been converted into the raster scan format, and generating the second image based on the second image signal that has been converted into the raster scan format.

\* \* \* \* \*